US008039485B2

(12) United States Patent
Redman-Furey et al.

(10) Patent No.: US 8,039,485 B2
(45) Date of Patent: Oct. 18, 2011

(54) MALATE SALTS, AND POLYMORPHS OF (3S,5S)-7-[3-AMINO-5-METHYL-PIPERIDINYL]-1-CYCLOPROPYL-1,4-DIHYDRO-8-METHOXY-4-OXO-3-QUINOLINECARBOXYLIC ACID

(75) Inventors: Nancy Lee Redman-Furey, Smyrna, NY (US); Jane Ellen Godlewski, Morris, NY (US); Michael Lloyd Dicks, Sherrill, NY (US)

(73) Assignee: Warner Chilcott Company, LLC, Fajardo, PR (US)

( * ) Notice: Subject to any disclaimer, the term of this patent is extended or adjusted under 35 U.S.C. 154(b) by 1088 days.

(21) Appl. No.: 11/728,343

(22) Filed: Mar. 26, 2007

(65) Prior Publication Data

US 2007/0232650 A1  Oct. 4, 2007

Related U.S. Application Data

(60) Provisional application No. 60/786,483, filed on Mar. 28, 2006.

(51) Int. Cl.
 *A61K 31/4709* (2006.01)
 *C07D 401/02* (2006.01)
(52) U.S. Cl. ........................................ 514/312; 546/156
(58) Field of Classification Search .................. 514/312; 546/156
 See application file for complete search history.

(56) References Cited

U.S. PATENT DOCUMENTS

| | | | |
|---|---|---|---|
| 4,017,622 A | 4/1977 | Minami et al. |
| 4,341,784 A | 7/1982 | Matsumoto et al. |
| 4,448,962 A | 5/1984 | Irikura et al. |
| 4,544,658 A | 10/1985 | Petersen et al. |
| 4,544,747 A | 10/1985 | Ishikawa et al. |
| 4,599,334 A | 7/1986 | Petersen et al. |
| 4,665,079 A | 5/1987 | Culbertson et al. |
| 4,771,054 A | 9/1988 | Domagala et al. |
| 4,780,468 A | 10/1988 | Bridges et al. |
| 4,822,801 A | 4/1989 | Domagala et al. |
| 4,844,902 A | 7/1989 | Grohe |
| 4,855,292 A | 8/1989 | Ueda et al. |
| 4,894,458 A | 1/1990 | Masuzawa et al. |
| 4,894,548 A | 1/1990 | Takahashi et al. |
| 4,920,120 A | 4/1990 | Domagala et al. |
| 4,988,709 A | 1/1991 | Ogata et al. |
| 4,990,517 A | 2/1991 | Petersen et al. |
| 4,994,599 A | 2/1991 | Chu |
| 4,997,946 A | 3/1991 | Edgar et al. |
| 5,043,450 A | 8/1991 | Masuzawa et al. |
| 5,051,509 A | 9/1991 | Nagano et al. |
| 5,072,001 A | 12/1991 | Hagen et al. |
| 5,098,912 A | 3/1992 | Hayakawa et al. |
| 5,116,834 A | 5/1992 | Domagala et al. |
| 5,157,117 A | 10/1992 | Takagi et al. |
| 5,229,396 A | 7/1993 | Brighty |
| 5,281,612 A | 1/1994 | Domagala et al. |
| 5,286,723 A | 2/1994 | Hayakawa et al. |
| 5,328,908 A | 7/1994 | Demuth, Jr. et al. |
| 5,348,961 A | 9/1994 | Iwata et al. |
| 5,364,861 A | 11/1994 | Hagen et al. |
| 5,387,748 A | 2/1995 | Demuth, Jr. et al. |
| 5,412,098 A | 5/1995 | Yasuhiro et al. |
| 5,457,104 A | 10/1995 | Bartel et al. |
| 5,464,796 A | 11/1995 | Petersen et al. |
| 5,480,879 A | 1/1996 | Petersen et al. |
| 5,519,016 A | 5/1996 | Kimura et al. |
| 5,547,962 A | 8/1996 | Ito et al. |
| 5,556,979 A | 9/1996 | Philipps et al. |
| 5,563,155 A | 10/1996 | Domagala et al. |
| 5,580,872 A | 12/1996 | Chu et al. |
| 5,599,816 A | 2/1997 | Chu et al. |
| 5,648,567 A | 7/1997 | Marhold et al. |
| 5,656,623 A | 8/1997 | White et al. |
| 5,726,182 A | 3/1998 | Chu et al. |
| 5,770,597 A | 6/1998 | Kim et al. |
| 6,235,751 B1 | 5/2001 | Park et al. |
| 6,329,391 B1 | 12/2001 | Ledoussal et al. |
| 6,387,928 B1 | 5/2002 | Ledoussal et al. |
| 6,645,981 B2 | 11/2003 | Ledoussal et al. |
| 6,803,469 B2 | 10/2004 | Randall |
| 6,849,740 B2 | 2/2005 | Ledoussal et al. |
| 6,900,224 B2 | 5/2005 | Ledoussal et al. |
| 7,019,143 B2 | 3/2006 | Ledoussal et al. |
| 7,456,279 B2 | 11/2008 | Reilly |
| 7,482,454 B2 | 1/2009 | Ledoussal et al. |
| 7,528,264 B2 * | 5/2009 | Hayes et al. .................. 548/534 |
| 2002/0049192 A1 | 4/2002 | Ledoussal et al. |

(Continued)

FOREIGN PATENT DOCUMENTS

CA 2073993 A1 1/1993

(Continued)

OTHER PUBLICATIONS

Lauderdale et al. "Comparative in vitro . . . " Antimicrob. agents and chemother. v.54(3) p. 1338-1342 (2010).*
Radem-furi et al. "Process for preparation . . . " CA 147:469244 (2007).*
Yokota et al. Chiral separation . . . ) J. Chem. Eng. Japan v. 37, p. 1284-1285 (2004).*
Zhang et al. "Racemic species . . . " J. Pharm. Sci. v.92, p. 1356-1366 (2003).*
Fasel et al. "Amplification of chirality . . . " Nature v. 439, p. 449-452 (2006).*
Braga et al. "Making crystals from . . . " Roy. soc. Chem.Chem. commun. p. 3635-3645 (2005).*

(Continued)

*Primary Examiner* — Celia Chang
(74) *Attorney, Agent, or Firm* — Fitzpatrick, Cella, Harper & Scinto

(57) ABSTRACT

The present invention is directed to malate salts of (3S,5S)-7-[3-amino-5-methyl-piperidinyl]-1-cyclopropyl-1,4-dihydro-8-methoxy-4-oxo-3-quinolinecarboxylic acid, and its polymorphs. The present invention is also directed to pharmaceutical compositions comprising the described salts and polymorphs.

17 Claims, 13 Drawing Sheets

U.S. PATENT DOCUMENTS

| | | |
|---|---|---|
| 2002/0173501 A1 | 11/2002 | Ledoussal et al. |
| 2003/0007862 A1 | 1/2003 | Ohtachi et al. |
| 2005/0101589 A1 | 5/2005 | Ledoussal et al. |
| 2006/0052359 A1 | 3/2006 | Grant et al. |
| 2006/0100436 A1 | 5/2006 | Ledoussal et al. |

FOREIGN PATENT DOCUMENTS

| | | |
|---|---|---|
| CA | 2152828 A1 | 7/1994 |
| CA | 2212226 A1 | 10/1995 |
| CA | 2217164 | 10/1996 |
| CA | 2238765 A1 | 5/1997 |
| CA | 2228536 | 8/1998 |
| CA | 2212007 C | 9/2004 |
| CL | 318-85 | 8/1985 |
| CN | 1086515 A | 5/1994 |
| CZ | 9201901 A3 | 1/1993 |
| CZ | 9302001 A3 | 4/1994 |
| CZ | 9400100 A3 | 3/1995 |
| EP | 0106489 A2 | 4/1984 |
| EP | 0195841 A1 | 1/1986 |
| EP | 0195316 A1 | 9/1986 |
| EP | 207497 A2 | 1/1987 |
| EP | 230295 A2 | 7/1987 |
| EP | 235762 A1 | 9/1987 |
| EP | 237955 | 9/1987 |
| EP | 0308019 A2 | 3/1989 |
| EP | 0342675 A2 | 11/1989 |
| EP | 0366189 A2 | 5/1990 |
| EP | 0413455 A2 | 2/1991 |
| EP | 443498 A1 | 8/1991 |
| EP | 0464823 A1 | 1/1992 |
| EP | 550016 A1 | 7/1993 |
| EP | 0572259 A1 | 12/1993 |
| EP | 0 641 793 A1 | 3/1995 |
| EP | 0775702 A1 | 5/1997 |
| EP | 0947513 A1 | 10/1999 |
| HU | 219910 B | 3/1993 |
| IT | 1279532 | 1/1997 |
| JP | 51-086476 | 7/1976 |
| JP | 61-205258 A | 9/1986 |
| JP | 61-225181 A | 10/1986 |
| JP | 01-056673 | 8/1987 |
| JP | 62-255482 | 11/1987 |
| JP | 64-016767 | 1/1989 |
| JP | 03-115277 A | 5/1991 |
| JP | 97244733 | 8/1991 |
| JP | 5-58895 A | 3/1993 |
| JP | 05-11-2554 A | 5/1993 |
| JP | 05-345777 | 12/1993 |
| JP | 07-48367 A | 2/1995 |
| JP | 8133977 | 5/1996 |
| JP | 09-002953 A | 1/1997 |
| JP | 09-052893 A | 2/1997 |
| JP | 10-287669 | 4/1997 |
| JP | 09-136886 | 5/1997 |
| JP | 97178847 | 6/1997 |
| JP | 97240318 | 8/1997 |
| JP | 11-12278 A | 1/1999 |
| JP | 11-60578 A | 3/1999 |
| JP | 3745433 B2 | 2/2006 |
| WO | 91/16894 A1 | 11/1991 |
| WO | 95/10519 A1 | 4/1995 |
| WO | 96/39407 A1 | 12/1996 |
| WO | WO 97/19072 A1 | 5/1997 |
| WO | WO 97/29102 | 8/1997 |
| WO | 98/52939 A1 | 11/1998 |
| WO | 98/54169 A1 | 12/1998 |
| WO | 99/07696 A1 | 2/1999 |
| WO | WO 99/14214 A1 | 3/1999 |
| WO | 00/21952 A1 | 4/2000 |
| WO | 00/78748 A1 | 12/2000 |
| WO | 01/53273 A1 | 7/2001 |
| WO | 02/48138 A1 | 6/2002 |
| WO | 2004/014893 A2 | 2/2004 |
| WO | WO 2005/033108 A | 4/2005 |

OTHER PUBLICATIONS

U.S. Appl. No. 10/085,786, filed Feb. 28, 2002, Ledoussal, et al.
U.S. Appl. No. 11/301,685, filed Dec. 13, 2005, Ledoussal, et al.
U.S. Appl. No. 11/728,342, filed Mar. 26, 2007, Reilly, Michael.
U.S. Appl. No. 11/728,341, filed Mar. 26, 2007, Hayes, Michael Patrick et al.
Bastin, Richard J., et al., "Salt Selection and Optimisation Procedures for Pharmaceutical New Chemical Entities," Organic Process Research & Development, 2000, vol. 4, pp. 427-435.
Albrecht, "Development of Antibacterial Agents of the Nalidixic Acid Type," Prog. In Drug Research, 21 (1977) pp. 9-104.
Berge, M., et al., "Pharmaceutical Salts," Journal of Pharmaceutical Sciences, Jan. 1977, vol. 66, No. 1, pp. 1-19.
Bouzard, et al., "Fluoronaphthyridines and Quinolones as Antibacterial Agents, 1. Synthesis and Structure-Activity Relationships of New 1-Substituted Derivatives", J.Med. Chem., 32 (1989), pp. 537-542.
Cecchetti, V., et al., "Potent 6-Desfluoro-8-methylquinolones as New Lead Compounds in Antibacterial Chemotherapy," J. Med. Chem., vol. 39, pp. 4952-4957 (1996).
Cecchetti, et al., "Studies on 6-Aminoquinolones: Synthesis and Antibacterial Evaluation of 6-Amino-8-methylquinolones", J. Med. Chem., 39 (1996) pp. 4952-4957.
Chemical Abstracts 96: 47559 1981 Otsuka.
Chemical Abstracts 120: 298485,1993, Ito.
Chemical Abstracts 126: 157539, 1994, Abstract by Bartel.
Chemical Abstracts 130: 223178, 1999, Tojima.
Chemical Abstracts 130: 124998, 1999, Yamamoto.
Chemical Abstracts 129: 343410, 1998, Takemura.
Chemical Abstracts 129: 153244, 1998, Sawa.
Cornett et al., "Chap. 14. Quinolone Antibacterial Agents", Annual Reports in Medicinal Chemistry, 1985, pp. 145-154.
Domagala et al., "7-Substituted 5-Amino-1 cyclopropyl-6,8-difluoro-1,4-dihyro-4oxo3-quinolinecarboxylic Acids: Synthesis and Biological Activity of a New Class of Quinolone Antibacterials", J. Med. Chem., 31 (1988), pp. 503-506.
Domagala et al., "Quinolone Antibacterials Containing the New 7-[3-(1-Aminoethyl)-1 pyrrolidinyl] Side Chain: The Effects of the 1-Aminoethyl Moiety and its Stereochemical Configurations on Potency and in Vivo Efficacy", J. Med. Chem. 36 (1993) pp. 871-882.
Domagala et al., "1-Substituted 7-[3-Ethylamino)methyl-1 pyrrolidinyl]-6,8-difluoro-1, 4-dihydro-4-oxo-3-quinoline carboxylic Acids. New Quantitative Structure-Activity Relationship at N 1 for the Quinolone Antibacterials", J. Med. Chem., 31 (1988), pp. 991-1001.
Fernandes et al., "Chap. 12 Quinolones", Annual Reports in Medicinal Chemistry, 1987, pp. 117-126.
Hagen, et al., "Synthesis and Antibacterial Activity of New Quinolones Containing a 7-[3-(1-Amino-1, methylethyl)-1-pyrrolidinyl] Moiety. Gram-Positive Agents with Excellent Oral Activity and Low Side-Effect potential", J. Med. Chem. 37 (1994), pp. 733-738.
Hayashi et al., "A Novel des-F(6)-Quinolone: Synthesis and In Vitro Activity of 7-(Isoindolin-5-y1) Derivatives", Abstracts in New Antimicrobials, 1997, p. 173; Poster Presentation.
Hong, et al., "Novel 5-Amino-6-methylquinolone Antibacterials: A New Class of Non-6-Fluoroquinolones", Bioorganic & Medicinal Chem. Letters, 7 (1997) pp. 1875-1878.
Klopman, et al., "Computer Automated Structure Evaluation of Uinolone Antibacterial Agents", Antimicrob. Agents Chemother., 31 (1987), pp. 1831-1840.
Koga, et al., "Structure-Activity Relationships of Antibacterial 6,7- and 7,8-Disubstituted 1-Alkyl-1,4-dihydro-4-oxoquinoline-3carboxylic Acids," J.Med. Chem., 23 (1980), pp. 1358-1363.
Ledoussal, et al., "Potent Non-6-Fluoro-Substituted Quinolone Antibacterials: Synthesis and Biological Activity", J. Med. Chem., 35 (1992), pp. 198-200.
Marpat 121: 31574, Lerchen, 1996.
Marpat 121: 57343, Kimura, 1993.
Marpat: 119: 56157, Nimura, 1993.
Marpat 111: 153779, Chiba, 1989.

Rodriguez-Spong, B., et al., "General Principles of Pharmaceutical Solid Polymorphism: A Supramolecular Perspective," Science Direct, Advanced Drug Delivery Reviews 56 (2004) pp. 241-274.

Rosen et al., "Asymmetric Synthesis and Properties of the Enantiomers of the Antibacterial Agent 7-(3-Aminopyrrolidin-1-y1)-1-(2,4-difluroophenyl)-1,4-dihydro-6-fluoro-4-oxo-1,8-naphthyridine-3-carboxylic Acid Hydrochloride", J. Med. Chem., 31 (1988), pp. 1586-1590.

Rosen et al., "Desing, Synthesis, and Properties of (4S)-7-4(Amino-2substituted-pyrrolidin 1-yl) quinolone-3-carboxylic Acids", J. Med. Chem., 31 (1988), pp. 1596-1622.

Sanchez, et al., "Quinolone Antibacterial Agents, Synthesis and Structure-Activity Relationships of 8-Substituted Quinoline-3-carboxylic Acids and 1,8 Naphthyridine-3-carboxylic Acids", J. Med. Chem., 31 (1988), pp. 983-991.

Tabarrini, Oriana et al., "6-Hydroxy Derivative as New Desluoroquinolone (DFQ): Synthesis and DNA-Binding Study", Nucleosides, Nucleotides & Nucleic Acids, vol. 19(8), 2000, pp. 1327-1336.

Wentland, et al., "Chap. 15. Quinolone Antibacterial Agents", Annual Reports in Medicinal Chemistry, 1985, pp. 145-154.

Wolfson et al., "The Fluoroquinolones: Structures, Mechanisms of Action and Resistance, and Specra of Activitiy In Vitro", Antimicrob. Agents Chemother., 28 (1985), pp. 581-586.

Xiam et al., "Synthesis and In Vitro Antibacterial Activity of Some 1-(Diluoromethoxphenyl) quinolone-3-carboxylic Acids", J. Pharm. Sciences. 78 (1989), pp. 585-588.

Brena-valle, L. J., "Synthesis of a New Chiral Amine: (S)-5, 5-dimethyl-2-methoxymethyl-pyrrolidine", Synthetic Communications, 31(5), pp. 697-706, (2001).

Casreact 145: 27827, Liu (2004).

Chemical Abstracts 121:157304, Marhold (1994).

Chemical Abstracts 121:157629, Philipps (1994).

Chemical Abstracts 126:26361, Cecchetti (1996).

Coudert, E. et al., "A Convenient and Efficient Synthesis of (2S, 4R)- and (2S, 4S)-4-Methylglutamic Acid", Synthesis, (8), pp. 862-865 (1997).

Hanessian, S. et al., "1, 3-Asymmetric Induction in dianionic Allylation Reactions of Amino Acid Derivatives-Synthesis of Functionally Useful Enantiopure Glutamates, Pipecolates and Pyroglutamates", Tetrahedron Letters, vol. 39, pp. 5887-5890 (1998).

Patani, G.A. et al., "Bioisosterism: A Rational Approach in Drug Design", Chem. Rev., vol. 96, pp. 3147-3176 (1996).

De Sarro, A. et al. "Effects of Novel 6-Desfluoroquinolones and Classic Quinolones on Pentylenetetrazole-Induced Seizures in Mice." Antimicrobial Agents Chemotherapy, pp. 1729-1736 (Jul. 1999).

Marpat 130:124998, Yamamoto (1999).

USPatFull 95:90528, Bartel (1995).

USPatFull 97:61894, Marhold (1997).

Suto, M.J. et al., "Fluoroquinolones: Relationships between Structural Variations, Mammalian Cell Cytotoxicity, and Antimicrobial Activity", J. Med. Chem., vol. 35, No. 25, pp. 4745-4750 (1992).

Li, Q. et al., "Synthesis and Structure—Activity Relationships of 2-Pyridones: A Novel Series of Potent DNA Gyrase Inhibitors as Antibacterial Agents", J. Med. Chem., vol. 39, pp. 3070-3088 (1996).

Sanders, Jr., W.E. et al., "Inducible beta-Lactamases: Clinical and Epidemiologic Implications for Use of Newer Cephalosporins", Reviews of Infectious Diseases, vol. 10, No. 4, pp. 830-838 (Jul.-Aug. 1988).

Ma, Z. et al., "Synthesis and Antimicrobial Activity of 4H-4-Oxoquinolizine Derivatives: Consequences of Structural Modification at the C-8 Position", J. Med. Chem., vol. 42, No. 20, pp. 4202-4213 (1999).

Jaen-Oltra, J. et al., "Artifical Neural Network Applied to Prediction of Fluorquinolone Antibacterial Activity by Topological Methods", J. Med. Chem., vol. 43, No. 6, pp. 1143-1148 (2000).

\* cited by examiner

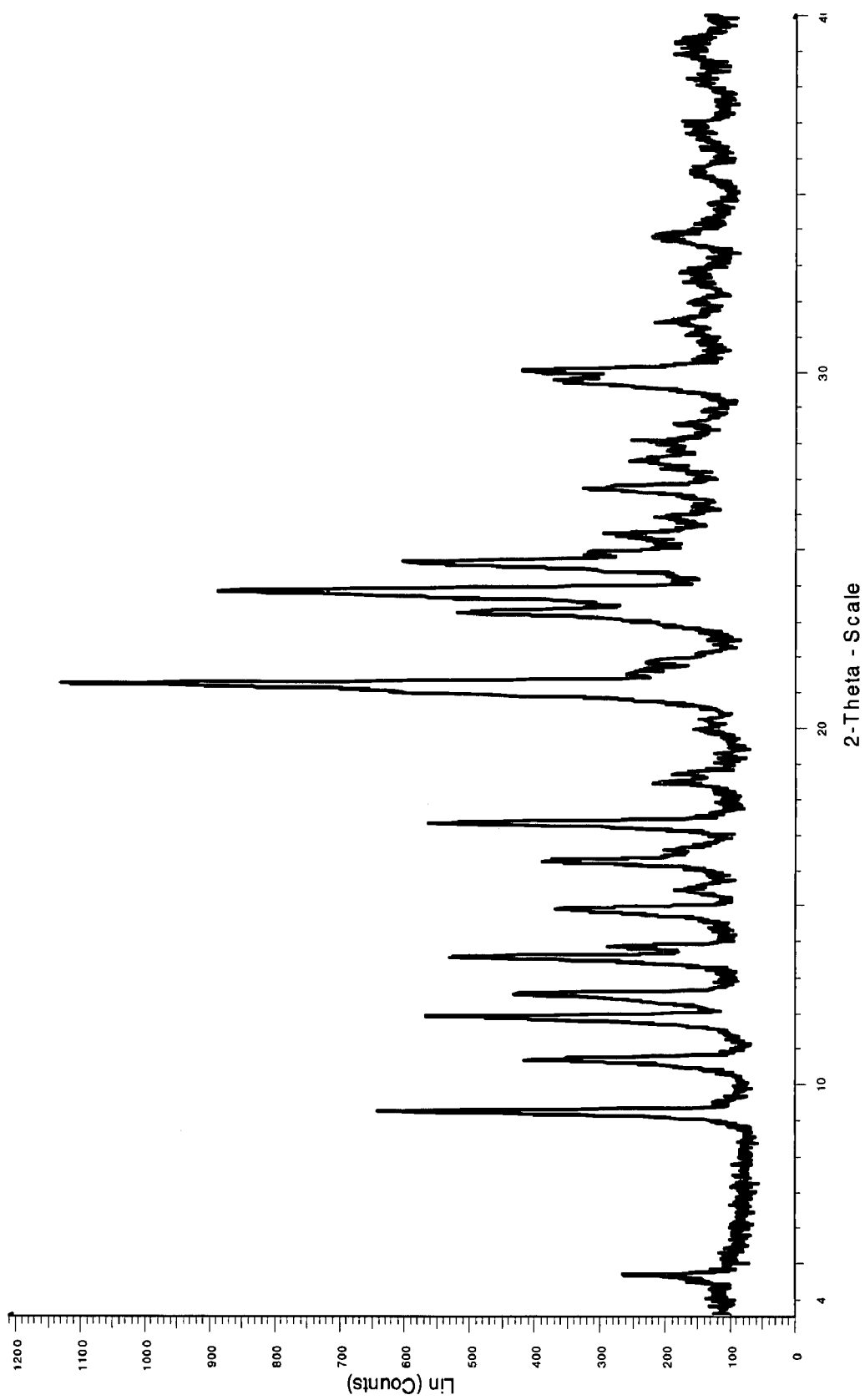
Figure 1. Representative X-ray Diffraction Pattern for D, L-malate hemi-hydrate

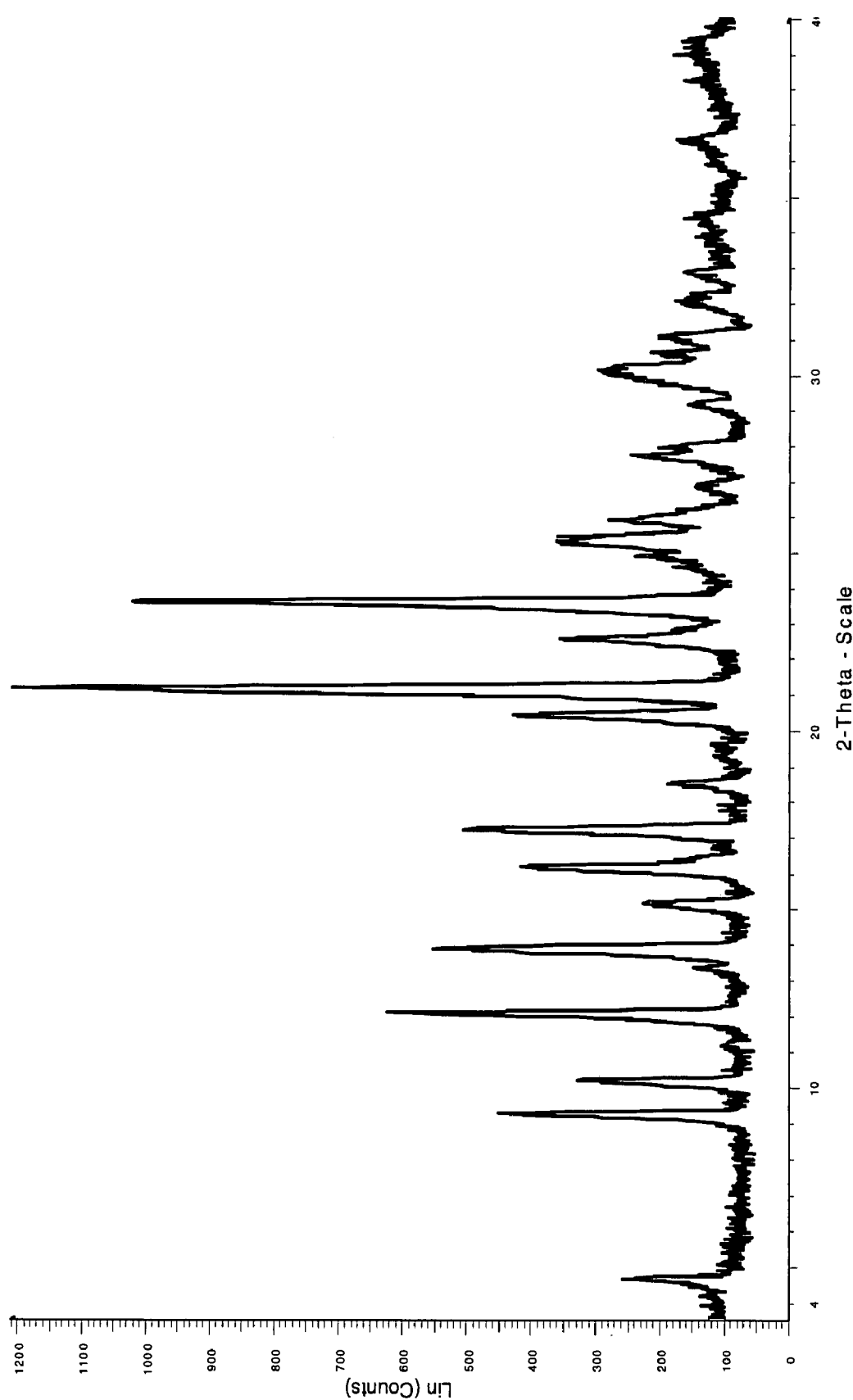
Figure 2. Representative X-ray Diffraction Pattern for D-malate hydrate

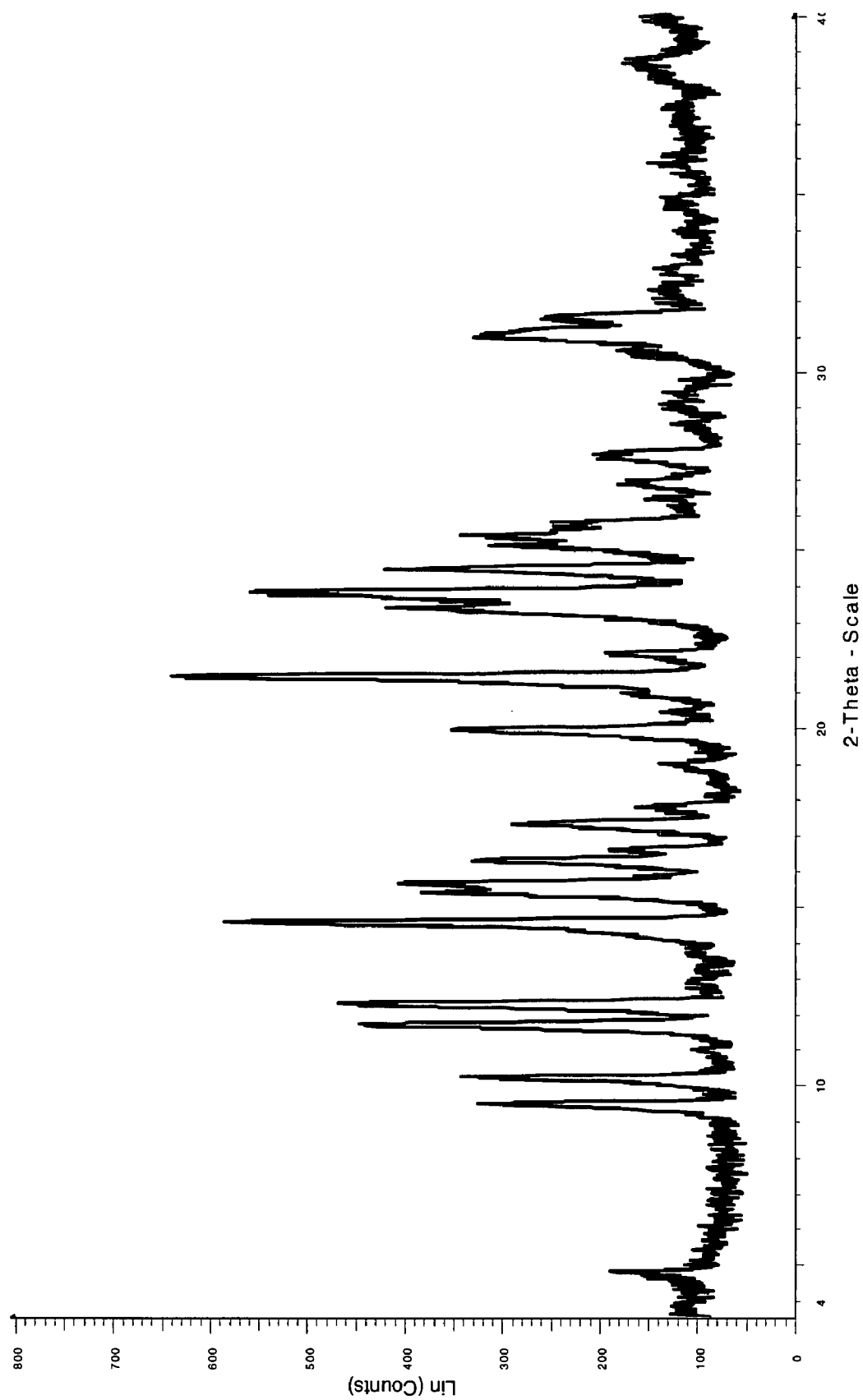
Figure 3. Representative X-ray Diffraction Pattern for L-malate hydrate

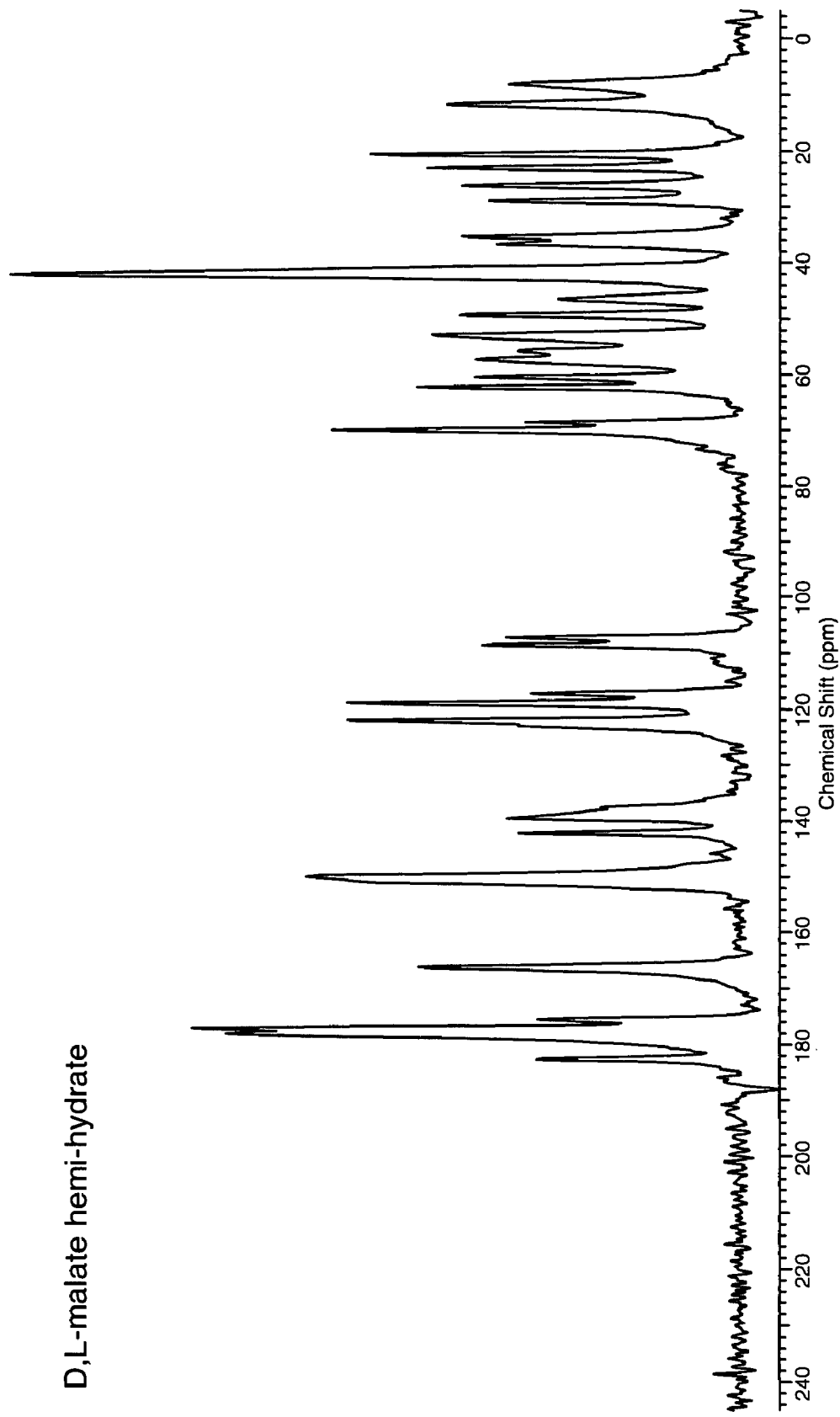
Figure 4. Representative NMR Spectra for D,L-malate hemi-hydrate

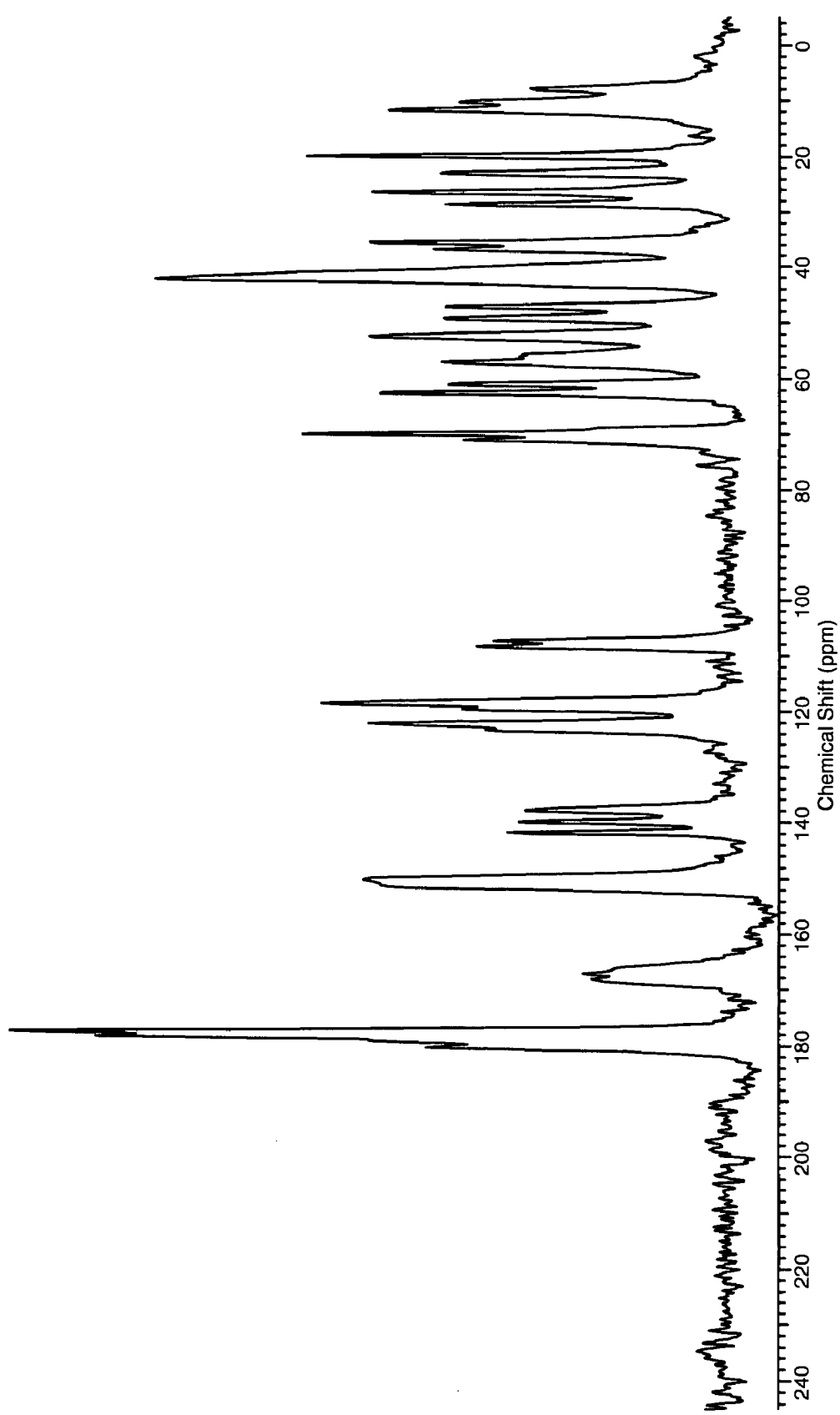
Figure 5. Representative NMR Spectra for D-malate hydrate

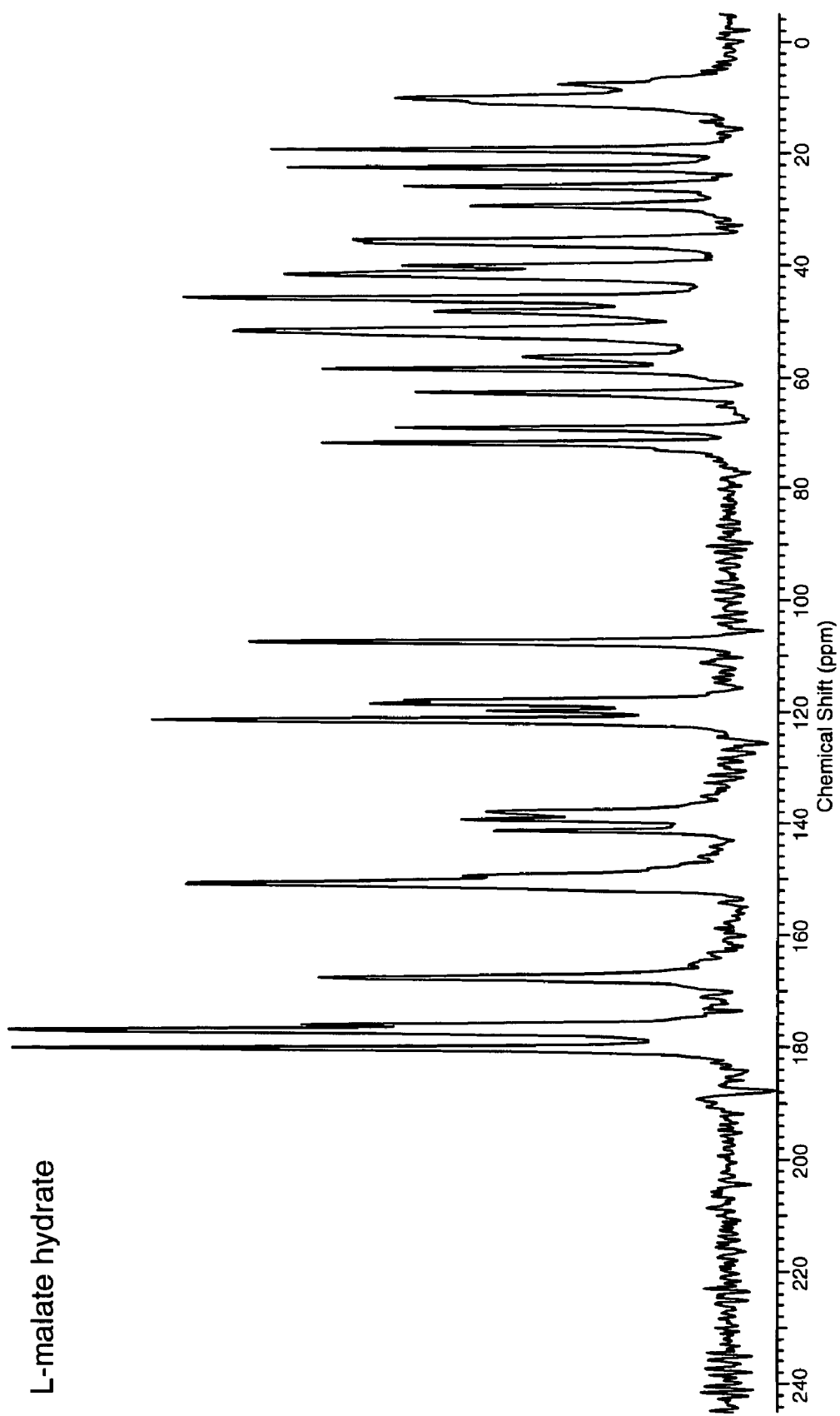
Figure 6. Representative NMR Spectra for L-malate hydrate

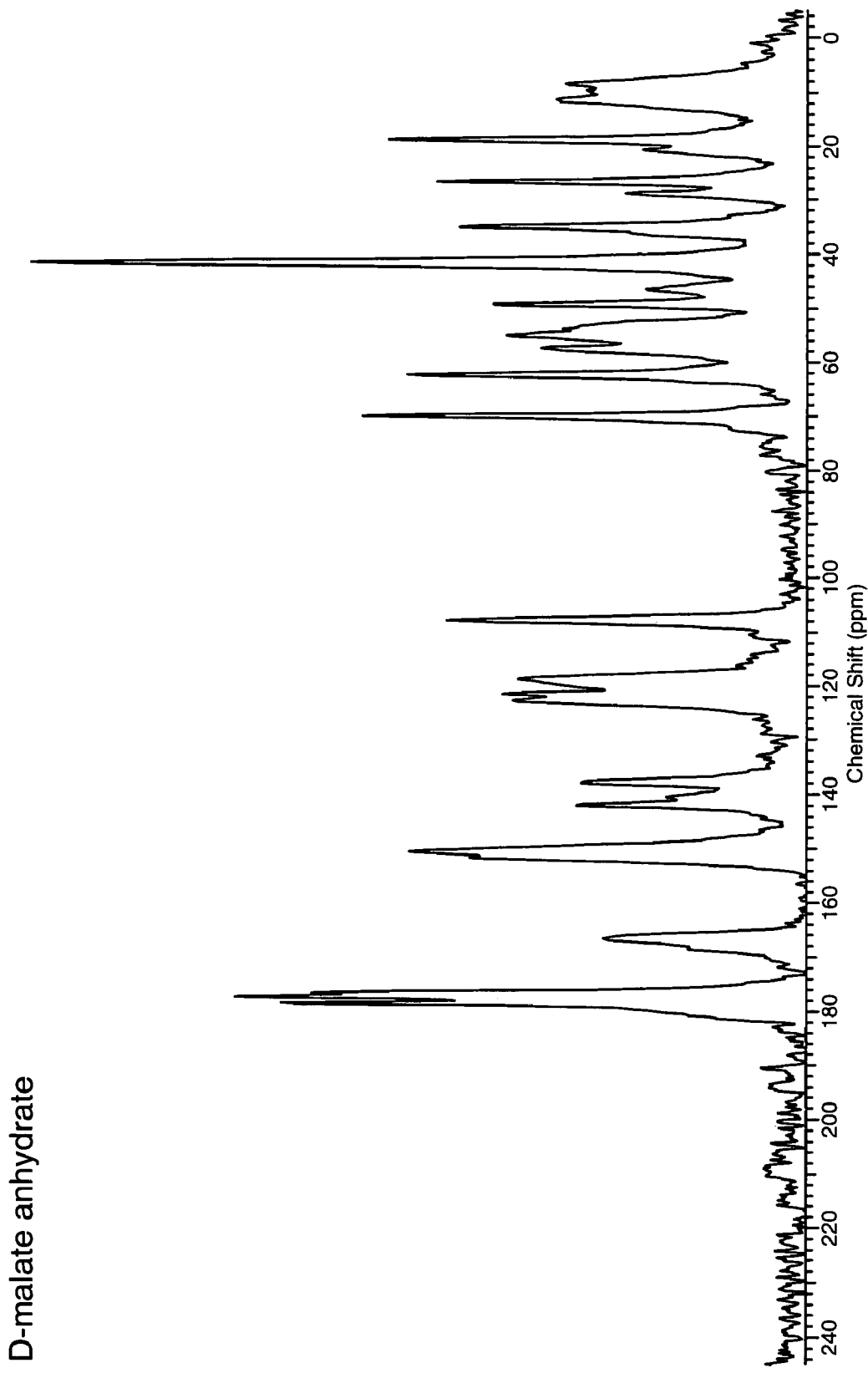

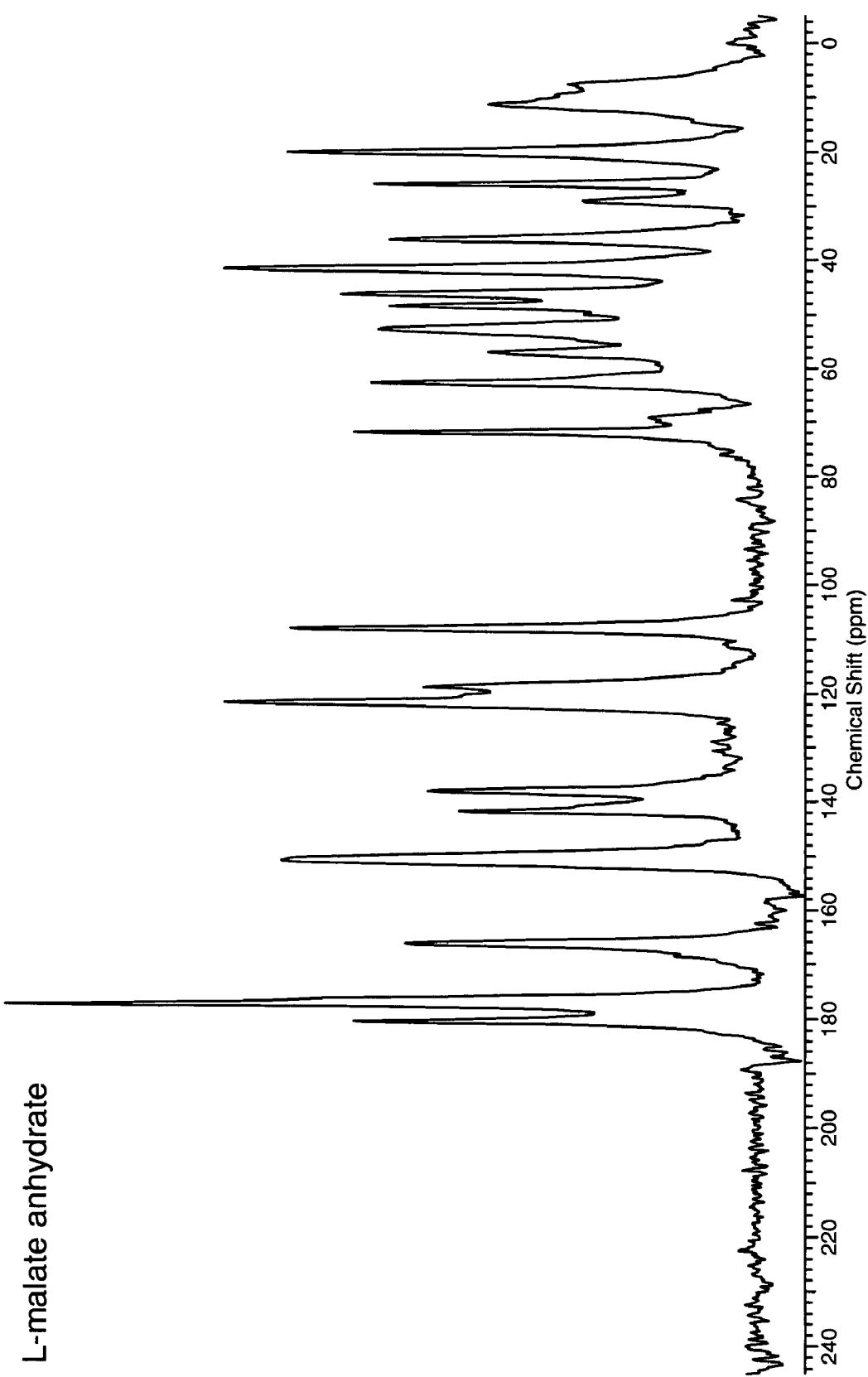
Figure 8. Representative NMR Spectra for L-malate anhydrate

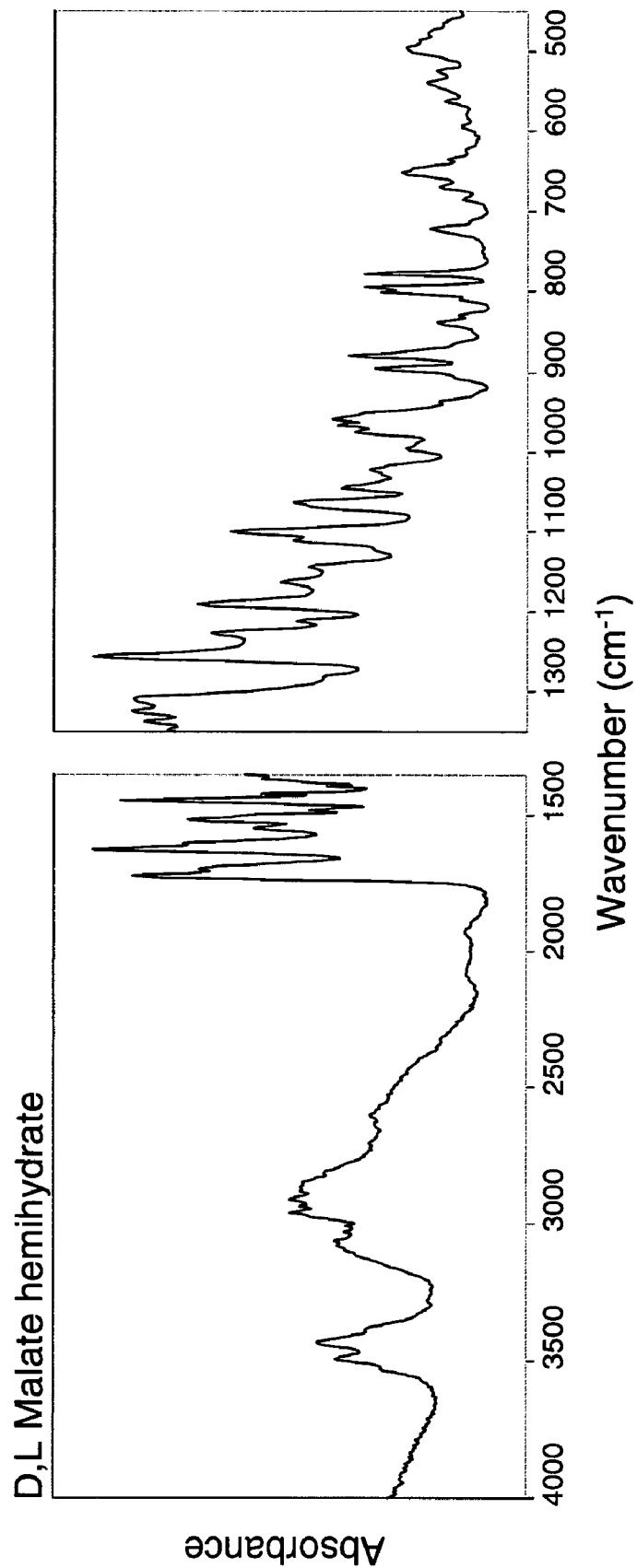
Figure 9. Representative IR Spectra for D,L-Malate Hemi-hydrate

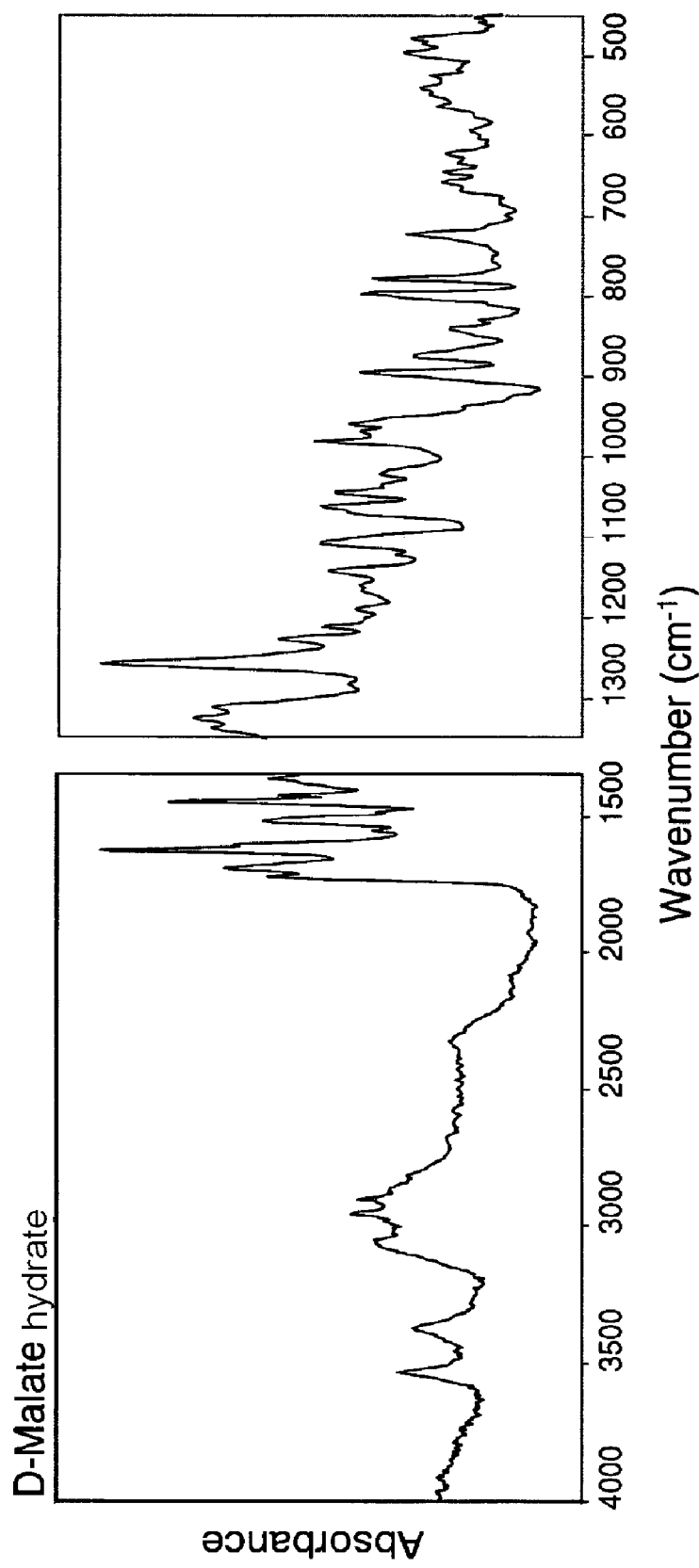
Figure 10. Representative IR Spectra for D-Malate Hydrate

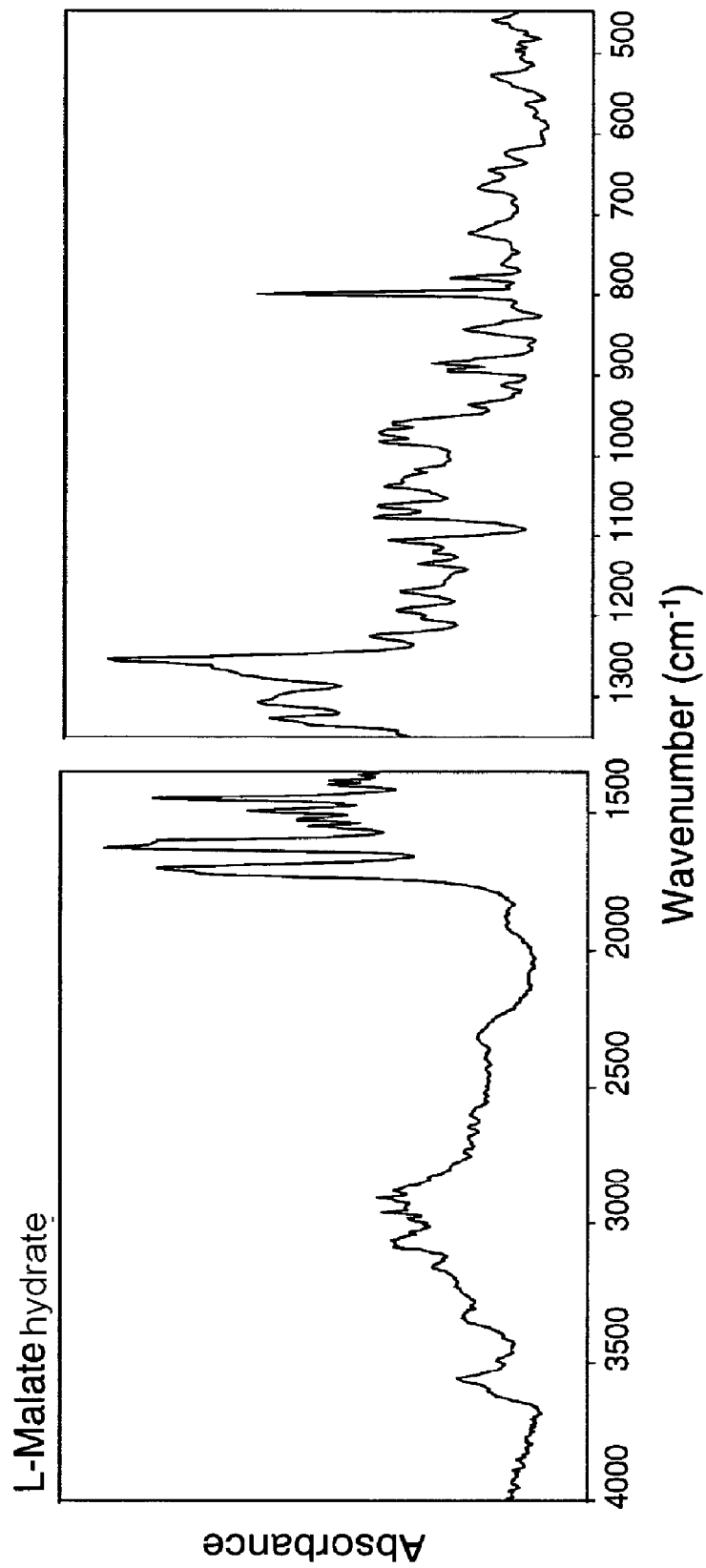
Figure 11. Representative IR Spectra for L-Malate Hydrate

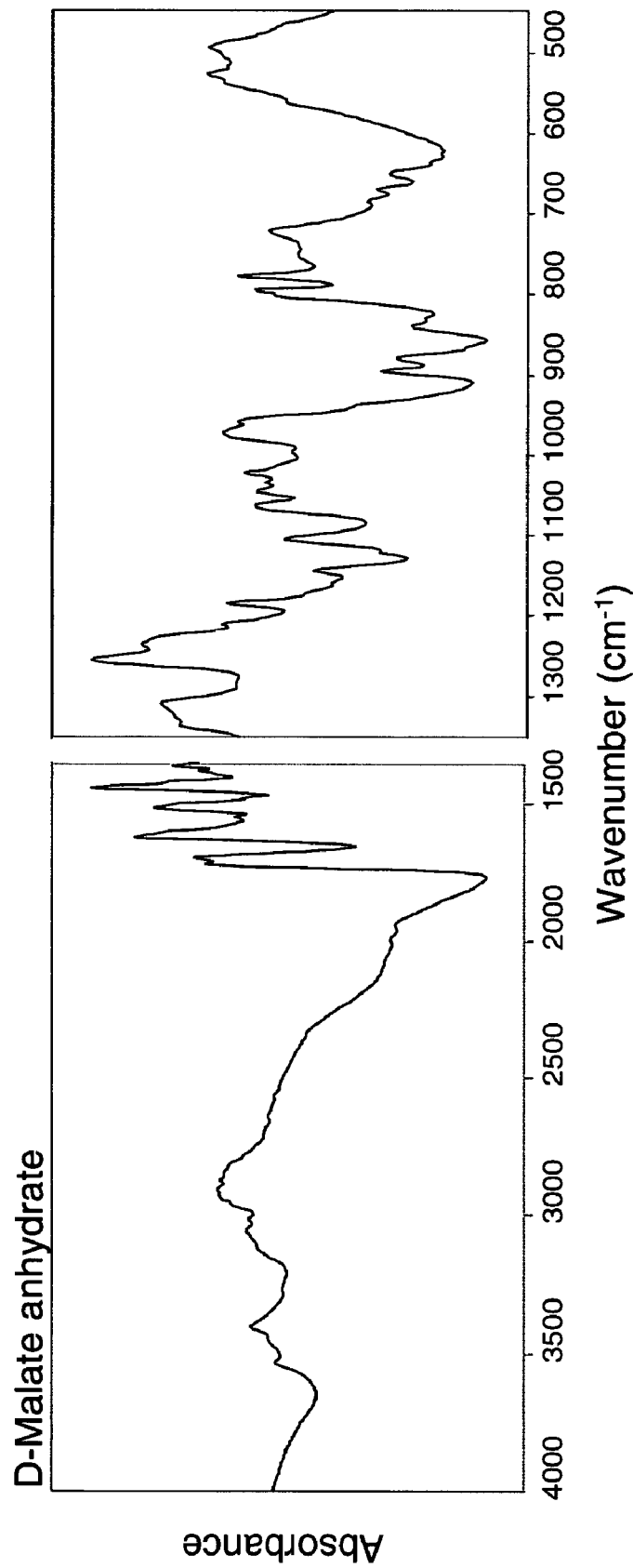
Figure 12. Representative IR Spectra for D-Malate Anhydrate

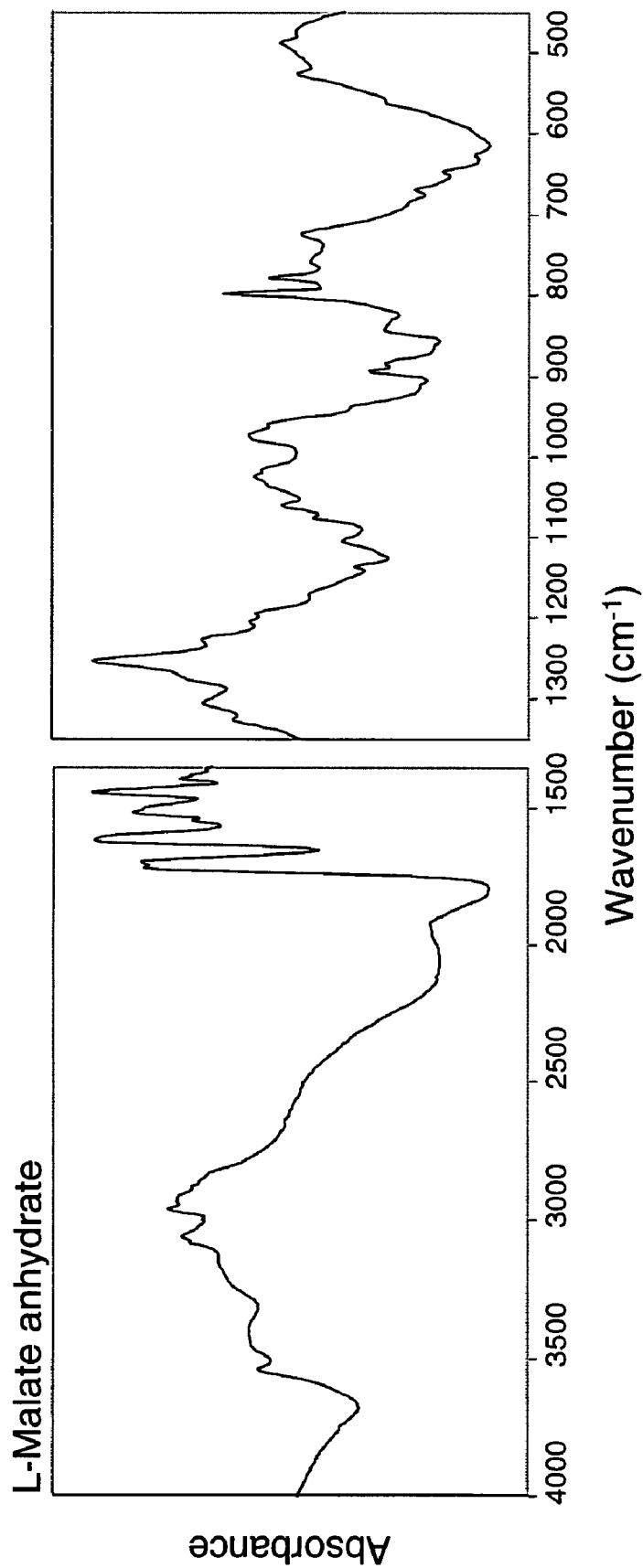
Figure 13. Representative IR Spectra for L-Malate Anhydrate

MALATE SALTS, AND POLYMORPHS OF (3S,5S)-7-[3-AMINO-5-METHYL-PIPERIDINYL]-1-CYCLOPROPYL-1,4-DIHYDRO-8-METHOXY-4-OXO-3-QUINOLINECARBOXYLIC ACID

CROSS REFERENCE TO RELATED APPLICATIONS

This application claims the benefit of U.S. Provisional Application No. 60/786,483, filed on Mar. 28, 2006.

FIELD OF THE INVENTION

The present invention is directed to malate salts and various polymorphic forms of malate salts of (3S,5S)-7-[3-amino-5-methyl-piperidinyl]-1-cyclopropyl-1,4-dihydro-8-methoxy-4-oxo-3-quinolinecarboxylic acid and pharmaceutical compositions thereof.

BACKGROUND OF THE INVENTION

The antimicrobial quinolone compounds, (3S,5S)-7-[3-amino-5-methyl-piperidinyl]-1-cyclopropyl-1,4-dihydro-8-methoxy-4-oxo-3-quinolinecarboxylic acid, and (3S,5R)-7-[3-amino-5-methyl-piperidinyl]-1-cyclopropyl-1,4-dihydro-8-methoxy-4-oxo-3-quinolinecarboxylic acid are disclosed in the U.S. Pat. No. 6,329,391, which is herein incorporated by reference in its entirety. Synthesis of various quinolone compounds have been reported in the literature, e.g., U.S. Pat. No. 6,329,391; U.S. Pat. No. 6,803,469; B. Ledoussal et al., "Non 6-Fluoro Substituted Quinolone Antibacterials: Structure and Activity", *J. Med. Chem.*, Vol. 35, p. 198-200 (1992); V. Cecchetti et al., "Studies on 6-Aminoquinolines: Synthesis and Antibacterial Evaluation of 6-Amino-8-methylquinolones", *J. Med. Chem.*, Vol. 39, pp. 436-445 (1996); V. Cecchetti et al., "Potent 6-Desfluoro-8-methylquinolones as New Lead Compounds in Antibacterial Chemotherapy", *J. Med. Chem.*, Vol. 39, pp. 4952-4957 (1996)).

The above-mentioned compounds are useful to treat microbial infections. However, what salt forms would yield a suitable preparation for the manufacture of a pharmaceutically acceptable composition is not known. Therefore, there is a need in the art to develop useful salt forms and polymorphs of these antimicrobial compounds.

SUMMARY OF THE INVENTION

In one aspect, the invention relates to malate salts of

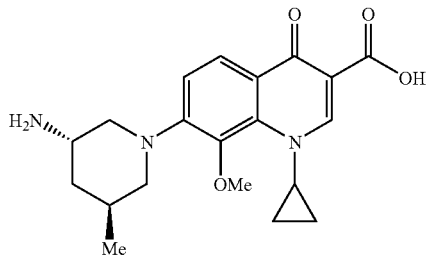

(3S,5S)-7-[3-amino-5-methyl-piperidinyl]-1-cyclopropyl-1, 4-dihydro-8-methoxy-4-oxo-3-quinolinecarboxylic acid (hereinafter Compound I, see also intermediate (23) in Section D, of Detailed Description of the Invention).

In one aspect, the invention relates to polymorphic malate salts of Compound I, wherein there is between about 0% and about 5% water by weight present.

In another aspect, the invention relates to a polymorphic salt of Compound I, wherein there is between about 1% and about 5% water by weight present.

In another aspect, the invention relates to a polymorphic salt of Compound I, wherein there is between about 0% and about 2% water by weight present.

In another aspect, the invention relates to a polymorphic salt of Compound I, having an X-ray diffraction pattern characterized substantially in accordance with the pattern of FIG. 1.

In another aspect, the invention relates to a polymorphic salt of Compound I, having an X-ray diffraction pattern characterized substantially in accordance with the pattern of FIG. 2.

In another aspect, the invention relates to a polymorphic salt of Compound I, having an X-ray diffraction pattern characterized substantially in accordance with the pattern of FIG. 3.

In another aspect, the invention relates to a polymorphic salt of Compound I, having a solid-state $^{13}$C NMR spectrum characterized substantially in accordance with the pattern of FIG. 4.

In another aspect, the invention relates to a polymorphic salt of Compound I, having a solid-state $^{13}$C NMR spectrum characterized substantially in accordance with the pattern of FIG. 5.

In another aspect, the invention relates to a polymorphic salt of Compound I, having a solid-state $^{13}$C NMR spectrum characterized substantially in accordance with the pattern of FIG. 6.

In another aspect, the invention relates to a polymorphic salt of Compound I, having a solid-state $^{13}$C NMR spectrum characterized substantially by in accordance with the pattern of FIG. 7.

In another aspect, the invention relates to a polymorphic salt of Compound I, having a solid-state $^{13}$C NMR spectrum characterized substantially in accordance with the pattern of FIG. 8.

In another aspect, the invention relates to a polymorphic salt of Compound I, having an infrared spectrum characterized substantially in accordance with the pattern of FIG. 9.

In another aspect, the invention relates to a polymorphic salt of Compound I, having an infrared spectrum characterized substantially in accordance with the pattern of FIG. 10.

In another aspect, the invention relates to a polymorphic salt of Compound I, having an infrared spectrum characterized substantially in accordance with the pattern of FIG. 11.

In another aspect, the invention relates to a polymorphic salt of Compound I, having an infrared spectrum characterized substantially in accordance with the pattern of FIG. 12.

In another aspect, the invention relates to a polymorphic salt of Compound I, having an infrared spectrum characterized substantially in accordance with the pattern of FIG. 13.

In another aspect, the invention relates to a polymorphic salt of Compound I, having characteristic X-ray diffraction peaks at about 10.7, about 11.98 and about 12.5 degrees 2 theta.

In another aspect, the invention relates to a polymorphic salt of Compound I, having characteristic X-ray diffraction peaks at about 9.3, about 12.1 and about 22.6 degrees 2 theta.

In another aspect, the invention relates to a polymorphic salt of Compound I, having characteristic X-ray diffraction peaks at about 9.5, about 11.7 and about 12.3 degrees 2 theta.

In another aspect, the invention relates to a polymorphic salt of selected from the group consisting of D,L-malate hemi-hydrate, D-malate hydrate, L-malate Hydrate, D-malate anhydrate, and L-malate anhydrate.

In another aspect, the invention relates to a pharmaceutical composition comprising a safe and effective amount of a polymorph according to any of the above-described polymorphs, and a pharmaceutically acceptable carrier.

In another aspect, the invention relates to a method of treating or preventing an infectious disorder in a human or other animal in need of such treatment, comprising: identifying a human or other animal in need of treating or preventing an infectious disorder; and administering to the human or other animal a safe and effective amount of compound according to claim 1.

BRIEF DESCRIPTION OF THE DRAWINGS

FIG. 1 shows a representative X-ray Diffraction Pattern for D,L-malate hemi-hydrate polymorph salt of Compound I.

FIG. 2 shows a representative X-ray Diffraction Pattern for D-malate hydrate polymorph salt of Compound I.

FIG. 3 shows a representative X-ray Diffraction Pattern for L-malate hydrate polymorph salt of Compound I.

FIG. 4 shows a representative solid-state $^{13}C$ NMR spectrum for D,L-malate hemi-hydrate polymorph salt of Compound I.

FIG. 5 shows a representative solid-state $^{13}C$ NMR spectrum for D-malate hydrate polymorph salt of Compound I.

FIG. 6 shows a representative solid-state $^{13}C$ NMR spectrum for L-malate hydrate polymorph salt of Compound I.

FIG. 7 shows a representative solid-state $^{13}C$ NMR spectrum for D-malate anhydrate polymorph salt of Compound I.

FIG. 8 shows a representative solid-state $^{13}C$ NMR spectrum for L-malate anhydrate polymorph salt of Compound I.

FIG. 9 shows a representative infrared spectrum for D,L-malate hemi-hydrate polymorph salt of Compound I.

FIG. 10 shows a representative infrared spectrum for D-malate hydrate polymorph salt of Compound I.

FIG. 11 shows a representative infrared spectrum for L-malate hydrate polymorph salt of Compound I.

FIG. 12 shows a representative infrared spectrum for D-malate anhydrate polymorph salt of Compound I.

FIG. 13 shows a representative infrared spectrum for L-malate anhydrate polymorph salt of Compound I.

DETAILED DESCRIPTION OF THE INVENTION

Herein are described various malate salts and different polymorphs of the malate salt. Selection of a pharmaceutically acceptable salt with desirable characteristics, e.g., solubility, stability, formulation ease, requires evaluation of many salts and resulting polymorphs (See Handbook of Pharmaceutical Salts, Properties, Selection and Use. Edited by P H Stahl, C. G. Wermuth (Wiley-VCH, Zurich, 2002)).

Solids exist in either amorphous or crystalline forms. In the case of crystalline forms, molecules are positioned in 3-dimensional lattice sites. When a compound crystallizes from a solution or slurry, it may crystallize with different spatial lattice arrangements, a property referred to as "polymorphism," with the different crystal forms individually being referred to as a "polymorph". Different polymorphic forms of a given substance may differ from each other with respect to one or more physical properties, such as solubility and dissolution rate, true density, crystal shape, compaction behavior, flow properties, and/or solid-state stability.

Crystallization

Manufacturing scale crystallizations are achieved by manipulating a solution so that the solubility limit for the compound of interest is exceeded. This may be achieved by a variety of methods, e.g., dissolving the compound at a relatively high temperature and then cooling the solution to below the saturation limit. Alternatively, the liquid volume may be reduced by boiling, ambient pressure evaporation, vacuum drying or by some other means. Solubility of the compound of interest may be decreased by the addition of an anti-solvent or a solvent in which the compound exhibits reduced solubility or a mixture of such solvents. Another option may be pH adjustment to reduce solubility. For detailed description on crystallization, please see Crystallization, $3^{rd}$ edition, J W Mullens, Butterworth-Heineman Ltd, 1993, ISBN 0750611294.

If salt formation is desired concurrent with crystallization, addition of the appropriate acid or base may result in direct crystallization of the desired salt, if salt is less soluble in the reaction media than the starting material. Likewise, completion of a synthetic reaction in a medium in which the final desired form is less soluble than the reactants may enable direct crystallization of the final product.

Optimization of the crystallization may include seeding of the crystallization medium with crystals of the desired form. In addition, many crystallization processes use combinations of the above-described strategies. An example would be the dissolution of the compound of interest in a solvent at high temperature, followed by controlled addition of an anti-solvent in a volume adequate to bring the system just below the saturation level. At this point, seeds of the desired form may be added, and with the seeds intact, the system is cooled to achieve the crystallization.

Pharmaceutical Formulations and Methods for Use

This invention also provides methods of treating or preventing an infectious disorder in a human or other animal subject, by administering a safe and effective amount of a salt or a polymorph to said subject. As used herein, an "infectious disorder" is any disorder characterized by the presence of a microbial infection. Preferred methods of this invention are for the treatment of bacterial infections. Such infectious disorders include (for example) central nervous system infections, external ear infections, infections of the middle ear (such as acute otitis media), infections of the cranial sinuses, eye infections, infections of the oral cavity (such as infections of the teeth, gums and mucosa), upper respiratory tract infections, lower respiratory tract infections, including pneumonia, genitourinary infections, gastrointestinal infections, gynecological infections, septicemia, sepsis, peritonitis, bone and joint infections, skin and skin structure infections, bacterial endocarditis, burns, antibacterial prophylaxis of surgery, and antibacterial prophylaxis in post-operative patients or in immunosuppressed patients (such as patients receiving cancer chemotherapy, or organ transplant patients).

The salts or polymorphs of the invention may be administered to treat or to prevent various microbial diseases. A pharmaceutical composition may comprise:

(a) a safe and effective amount of a salt or a polymorph of the invention; and (b) a pharmaceutically-acceptable carrier.

The term "treatment" is used herein to mean that administration of a compound of the present invention mitigates a disease or a disorder in a host. Thus, the term "treatment" includes, preventing a disorder from occurring in a host, particularly when the host is predisposed to acquiring the disease, but has not yet been diagnosed with the disease; inhibiting the disorder; and/or alleviating or reversing the disorder. Insofar as the methods of the present invention are directed to preventing disorders, it is understood that the term "prevent" does not require that the disease state be completely thwarted. (See Webster's Ninth Collegiate Dictionary.) Rather, as used herein, the term preventing encompasses to the ability of the skilled artisan to identify a population that is susceptible to disorders, such that administration of the compounds of the present invention may occur prior to onset of a disease. The term does not imply that the disease state be completely avoided. The compounds identified by the screening methods of the present invention may be administered in conjunction with other compounds.

Safety and therapeutic efficacy of compounds identified may be determined by standard procedures using in vitro or in vivo technologies. Compounds that exhibit sufficient therapeutic indices may be preferred, although compounds with otherwise insufficient therapeutic indices may also be useful. The data obtained from the in vitro and in vivo toxicological and pharmacological techniques may be used to formulate the range of doses. Effectiveness of a compound may further be assessed either in animal models or in clinical trials of patients.

A "safe and effective amount" of a compound of the invention is an amount that is effective, to inhibit microbial growth at the site of an infection to be treated in a host, with acceptable side effects (such as toxicity, irritation, or allergic response). The specific "safe and effective amount" will vary with such factors as the particular condition being treated, the physical condition of the patient, the duration of treatment, the nature of concurrent therapy (if any), the specific dosage form to be used, the excipients(s) employed, and the dosage regimen desired for the composition.

As used herein, "pharmaceutically acceptable carrier" is intended to include solvents, dispersion media, coatings, antibacterial and antifungal agents, isotonic and absorption delaying agents, and the like, compatible with pharmaceutical administration. The use of such media and agents for pharmaceutically active substances is known in the art. Except insofar as any conventional media or agent is incompatible with the compound, such media may be used in the compositions of the invention. Supplementary compounds may also be incorporated into the compositions. A pharmaceutical composition of the invention is formulated to be compatible with its intended route of administration. Examples of routes of administration include parenteral, (e.g., intravenous, intradermal, subcutaneous, intramuscular), oral, inhalation, transdermal (topical), transmucosal, and rectal administration. Solutions or suspensions used for parenteral, intradermal, or subcutaneous application may include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH may be adjusted with suitable acids or bases. The parenteral preparation may be enclosed in ampoules, disposable syringes or multiple dose vials made of glass or plastic.

Pharmaceutical compositions suitable for injectable use include sterile aqueous solutions (where water-soluble) or dispersions and sterile powders for the extemporaneous preparation of sterile injectable solutions or dispersion. For intravenous administration, suitable carriers include saline, Cremophor EL™ (BASF, Parsippany, N.J.) or phosphate buffered saline (PBS). The composition may be sterile and be fluid to the extent that easy syringability exists. It should be stable under the conditions of manufacture and storage and should be preserved against the contaminating action of microorganisms such as bacteria and fungi. The carrier may be a solvent or dispersion medium containing, e.g., water, ethanol, polyol (for example, glycerol, propylene glycol, and polyethylene glycol), and suitable mixtures thereof. The fluidity may be maintained, e.g., by the use of a coating such as lecithin, by the maintenance of the required particle size in the case of dispersion, and by the use of surfactants. Prevention of the microbial growth may be achieved by various antibacterial and antifungal agents, e.g., parabens, chlorobutanol, phenol, ascorbic acid, thimerosal. Isotonic agents may be included, e.g., sugars, polyalcohols such as mannitol, sorbitol, and sodium chloride. Prolonged absorption of the injectable compositions may be achieved by including in the composition an agent that delays absorption, for example, aluminum monostearate and gelatin.

Sterile injectable solutions may be prepared by incorporating the compound in the required amount in an appropriate solvent with one or a combination of ingredients enumerated above followed by filtered sterilization. Dispersion media may be prepared by incorporating the compound into a sterile vehicle that may contain a basic dispersion medium and other ingredients. In the case of sterile powders for the preparation of sterile injectable solutions, preferred methods of preparation include vacuum drying and freeze-drying which yields a powder of the compound plus any additional desired ingredients from a previously sterile-filtered solution thereof.

Oral compositions may include an inert diluent or an edible carrier. They may be enclosed in gelatin capsules or compressed into tablets. For oral administration, the agent may be contained in enteric forms to survive the stomach, or further coated or mixed for a release in a particular region of the GI tract by known methods. For the purpose of oral therapeutic administration, the compound may be incorporated with excipients and used in the form of tablets, troches, or capsules. Oral compositions may also be prepared using a fluid carrier for use as a mouthwash, wherein the compound in the fluid carrier is applied orally and swished and expectorated or swallowed. Pharmaceutically compatible binding agents, and/or adjuvant materials may be included as part of the composition. The tablets, pills, capsules, troches and the like may contain any of the following ingredients, or compounds of a similar nature: a binder such as microcrystalline cellulose, gum tragacanth or gelatin; an excipient such as starch or lactose, a disintegrating agent such as alginic acid, Primogel™, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

For administration by inhalation, the compounds may be delivered in the form of an aerosol spray from pressured container or dispenser, which contains a suitable propellant, e.g., a gas such as carbon dioxide, or a nebulizer.

Systemic administration may also be by transmucosal or transdermal means. For transmucosal or transdermal administration, penetrants appropriate to the barrier to be permeated may be used in the formulation. Such penetrants are generally known in the art, and include, for example, for transmucosal administration, detergents, bile salts, and fusidic acid derivatives. Transmucosal administration may be accomplished using nasal sprays or suppositories. For transdermal administration, the compounds may be formulated into ointments, salves, gels, or creams as generally known in the art.

The compounds may also be prepared in the form of suppositories (e.g., with conventional suppository bases such as cocoa butter and other glycerides) or retention enemas for rectal delivery.

In one embodiment, the compounds are prepared with carriers that will protect the compound against rapid elimination from the body, such as a controlled release formulation, including implants and microencapsulated delivery systems. Biodegradable, biocompatible polymers may be used, such as ethylene vinyl acetate, polyanhydrides, polyglycolic acid, collagen, polyorthoesters, and polylactic acid. Methods for preparation of such formulations will be apparent to those skilled in the art. Liposomal suspensions may also be used as pharmaceutically acceptable carriers.

It may be advantageous to formulate oral or parenteral compositions in dosage unit form for ease of administration and uniformity of dosage. "Dosage unit form" as used herein refers to physically discrete units suited as unitary dosages for the subject to be treated, each unit containing a predetermined quantity of compound calculated to produce the desired therapeutic effect in association with a pharmaceutical carrier. The specification for the dosage unit forms of the invention may be dictated by and may be dependent on the characteristics of the compound and the particular therapeutic effect to be achieved, and the limitations inherent in the art of preparing such a compound for the treatment of animals.

EXAMPLES

Example 1

Synthesis of (3S,5S)-7-[3-amino-5-methyl-piperidinyl]-1-cyclopropyl-1,4-dihydro-8-methoxy-4-oxo-3-quinolinecarboxylic acid and malate salt thereof A. Synthesis of (3S,5S)-(5-Methyl-piperidin-3-yl)-carbamic acid tert-butyl ester (8)

with external cooling to maintain temperature at <30°. The resulting solution is stirred at 25° C.+5° C. for 1.0 hour, after which the methanol is distilled off under reduced pressure. The resulting thick oil is azeotroped with ethyl acetate (3×2.5 L) to remove residual methanol. The residue is dissolved in ethyl acetate (27.4 L), charged into a 50 L reactor, and neutralized by the addition of triethylamine (3.6 Kg) from an addition funnel over 30 minutes. The temperature of the neutralization is maintained below 30° C. via external cooling. The resulting suspension of triethylamine hydrochloride is removed by filtration, and the clarified mother liquor solution is charged to a 50 L reactor, along with DMAP (0.53 Kg). Di-tert-butyl dicarbonate (8.43 Kg) is added via hot water heated addition funnel, over a period of 30 min with external cooling to maintain temperature at about 20-30° C. The reaction is complete after 1 hour as determined by TLC analysis. The organic phase is washed with ice cold 1N HCl (2×7.5 L), saturated sodium bicarbonate solution (1×7.5 L), and dried over magnesium sulfate. The mixture is filtered through a nutsche filter and ethyl acetate is removed under reduced pressure to yield a crystalline slurry that is triturated with MTBE (10.0 L) and filtered to afford intermediate (2) as a white solid (5.45 Kg, 52.4%). Anal. Calcd for $C_{11}H_{17}NO_5$: C, 54.3; H, 7.04; N, 5.76. Found: C, 54.5; H, 6.96; N, 5.80. HRMS (ESI+) Expected for $C_{11}H_{18}NO_5$, [M+H] 244.1185. Found 244.1174; $^1$H NMR (CDCl$_3$, 500 MHz):δ=4.54 (dd, J=3.1, 9.5 Hz, 1H), 3.7 (s, 3H), 2.58-2.50 (m, 1H), 2.41 (ddd, 1H, J=17.6, 9.5, 3.7), 2.30-2.23 (m, 1H), 1.98-1.93 (m, 1H), 1.40 (s, 9H); $^{13}$C NMR (CDCl$_3$, 125.70 MHz) δ 173.3, 171.9, 149.2, 83.5, 58.8, 52.5, 31.1, 27.9, 21.5; Mp 70.2° C.

(2S,4E)-1-(1,1-Dimethylethyl)-4-[(dimethylamino)methylene]-5-oxo-1,2-pyrrolidinedicarboxylic acid-2-methyl

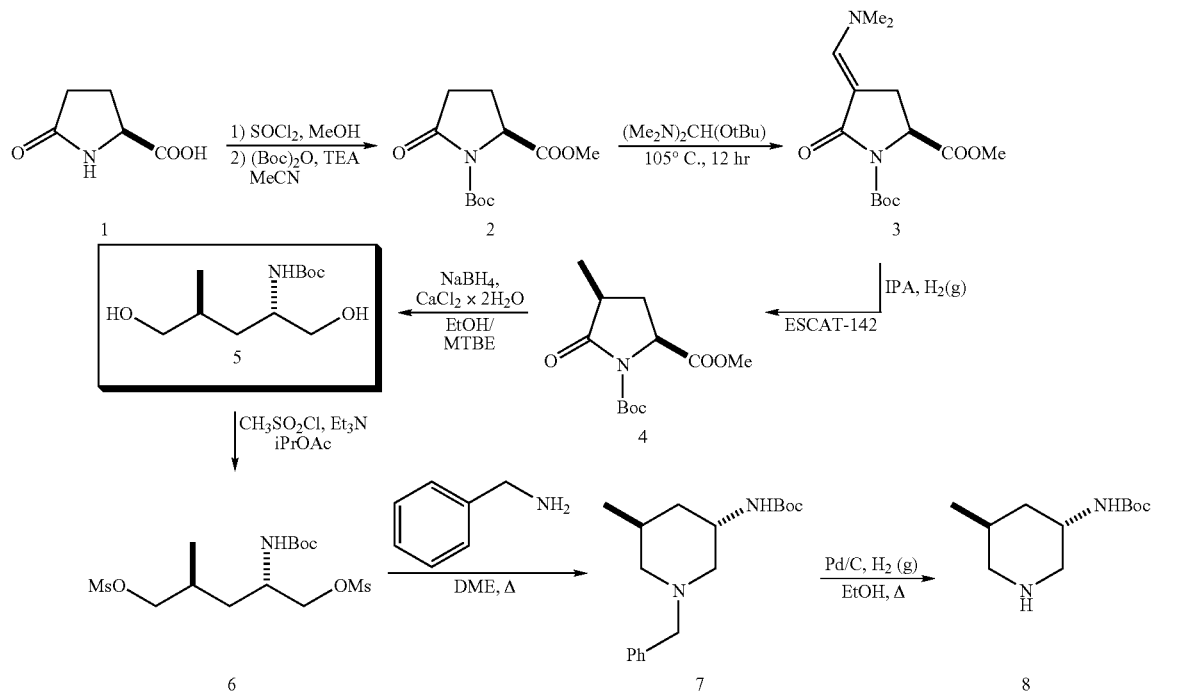

(2S)-1-(1,1-Dimethylethyl)-5-oxo-1,2-pyrrolidinedicarboxylic acid-2-methyl ester, (2). A 50-L reactor is charged with compound (1) (5.50 Kg, 42.60 mol), methanol (27 L) and cooled to 10-15° C. Thionyl chloride (10.11 Kg, 2.0 equiv.) is added via addition funnel over a period of 65 min, ester (3). A 50-L reactor is charged with intermediate (2) (7.25 Kg, 28.8 mol), DME (6.31 Kg), and Bredereck's Reagent (7.7 Kg, 44.2 mole). The solution is agitated and heated to 75° C.±5° C. for at least three hours. The progress of the reaction is monitored by HPLC. The reaction is cooled to 0° C.±5° C. over on hour during which time a precipitate forms. The mixture is held at 0° C.±5° C. for one hour and filtered though a nutsche filter and the product dried in a vacuum oven for at least 30 hours at 30° C.±5° C. to give intermediate (3) as a white crystalline solid (6.93 Kg, 77.9%). Anal. Calcd for $C_{14}H_{22}N_2O_5$: C, 56.4; H, 7.43; N, 9.39. Found C, 56.4; H, 7.32; N, 9.48; HRMS (ESI+) Expected for $C_{14}H_{22}N_2O_5$, [M+H] 299.1607. Found 299.1613; $^1$H NMR (CDCl$_3$, 499.8 MHz)δ=7.11 (s, 1H), 4.54 (dd, 1H, J=10.8, 3.6), 3.74 (s, 3H), 3.28-3.19 (m, 1H), 3.00 (s, 6H), 2.97-2.85 (m, 1H), 1.48 (s, 9H); $^{13}$C NMR (CDCl$_3$, 125.7 MHz) δ=172.6, 169.5, 150.5, 146.5, 90.8, 82.2, 56.0, 52.3, 42.0, 28.1, 26.3. Mp 127.9° C.

(2S,4S)-1-(1,1-Dimethylethyl)-4-methyl-5-oxo-1,2-pyrrolidinedicarboxylic acid-2-methyl ester (4). A 10-gallon Pfaudler reactor is inerted with nitrogen and charged with ESCAT 142 5% palladium powder on carbon (50% wet, 0.58 Kg wet wt.), intermediate (3) (1.89 Kg, 6.33 mol) and isopropanol (22.4 Kg). The reaction mixture is agitated under a 45-psi hydrogen atmosphere at 45° C. for 18 hrs. The reaction mixture is then cooled to room temperature and filtered though a bed of Celite (0.51 Kg) in a nutsche filter to remove catalyst. The mother liquor is evaporated under reduced pressure to give a thick oil that crystallizes on standing to afford 4 (1.69 Kg, 100%) as a 93:7 diastereomeric mixture. A sample of product mixture is purified by preparative HPLC to give material for analytical data. Anal. Calcd for $C_{12}H_{19}NO_5$: C, 56.0; H, 7.44; N, 5.44. Found C, 55.8; H, 7.31; N, 5.44; MS (ESI+) Expected for $C_{12}H_{19}NO_5$, [M+H] 258.1342. Found 258.1321; $^1$H NMR (CDCl$_3$, 499.8 MHz) δ=4.44 (m, 1H), 3.72 (s, 3H), 2.60-2.48 (m, 2H), 1.59-1.54 (m, 1H), 1.43 (s, 9H), 1.20 (d, j=6.8 Hz,3H); $^{13}$C NMR (CDCl$_3$, 125.7 MHz) δ=175.7, 172.1, 149.5, 83.6, 57.4, 52.5, 37.5, 29.8, 27.9, 16.2. Mp 89.9° C.

(1S,3S)-(4-Hydroxyl-1-hydroxymethyl-3-methyl-butyl)-carbamic acid tert-butyl ester (5). A 50-L reactor is charged with intermediate (4) (3.02 Kg, 11.7 mol), absolute ethanol (8.22 Kg), and MTBE (14.81 Kg). The solution is agitated and cooled to 0° C.±5° C. and sodium borohydride (1.36 Kg, 35.9 mol) is added in small portions so as to maintain reaction temperature at 0° C.±5° C. A small amount of effervescence is observed. The reaction mixture is warmed to 10° C.±5° C. and calcium chloride dihydrate (2.65 Kg) is added portion wise at a slow rate over an hour so as to maintain a reaction temperature of 10° C.±5° C. The reaction is allowed to warm to 20° C.±5° C. over one hour and agitated for an additional 12 hours at 20° C.±5° C. The reaction is cooled to −5° C.±5° C., ice-cold 2N HCl (26.9 Kg) is added at a rate to maintain a reaction temperature of 0° C.±5° C. Agitation is stopped to allow phases to separate. The lower aqueous phase (pH=1) is removed. The reactor is charged with aqueous saturated sodium bicarbonate (15.6 Kg) over five minutes. Agitation is stopped to allow phases to separate. The lower aqueous phase (pH=8) is removed. The reactor is charged with magnesium sulfate (2.5 Kg) and agitated for at least 10 minutes. The mixture is filtered though a nutsche filter, and condensed under reduced pressure to afford intermediate (5) (1.80 Kg, 66%). Anal. Calcd for $C_{11}H_{23}NO_4$: C, 56.6; H, 9.94; N, 6.00. Found C, 56.0; H, 9.68; N, 5.96; HRMS (ESI+) Expected for $C_{11}H_{24}NO_4$, [M+H] 234.1705. Found 234.1703; $^1$H NMR (CDCl$_3$, 500 MHz) δ=6.34(d, J=8.9 Hz, 1H, NH), 4.51 (t, J=5.8, 5.3 Hz, 1H, NHCHCH$_2$OH), 4.34 (t, J=5.3, 5.3 Hz, 1H, CH3CHCH$_2$OH), 3.46-3.45, (m, 1H, NHCH), 3.28 (dd, J=10.6, 5.3 Hz, NHCHCHHOH), 3.21 (dd, J=10.2, 5.8 Hz, 1H, CH$_3$CHCHHOH), 3.16 (dd, J=10.2, 6.2 Hz, 1H, NHCHCHHOH), 3.12 (dd, J=10.6, 7.1 Hz, 1H, CH$_3$CHCH HOH), 1.53-1.50 (m, 1H, CH$_3$CHCHHOH), 1.35 (s, 9H, O(C H$_3$)$_3$, 1.30 (ddd, J=13.9, 10.2, 3.7 Hz, 1H, NHCHCHHCH), 1.14 (ddd, J=13.6, 10.2, 3.4 Hz, 1H, NHCHCHHCH), 0.80 (d, J=6.6 Hz, 3H, CH$_3$); $^{13}$C NMR (CDCl$_3$, 125.7 MHz) δ 156.1, 77.9, 50.8, 65.1, 67.6, 65.1, 35.6, 32.8, 29.0, 17.1. Mp 92.1° C.

(2S,4S)-Methanesulfonic acid 2-tert-butoxycarbonylamino-5-methanesulfonyloxy-4-methyl-pentyl ester (6). A 50 L reactor is charged with a solution of intermediate (5) (5.1 Kg) in isopropyl acetate (i-PrOAc) 11.8 Kg followed by a rinse with an additional 7.9 Kg i-PrOAc. The reaction is cooled to 15° C.±5° C. and triethylamine (TEA) (7.8 Kg) is added while maintaining the set temperature. The reactor is further cooled to 0° C.±5° C. and methanesulfonyl chloride (MsCl) (6.6 Kg) is added to the reaction solution while maintaining the set temperature. The reaction is stirred for a few hours and monitored for completion by HPLC or TLC. The reaction is quenched by the addition of a saturated aqueous bicarbonate solution and the resulting isolated organic phase is washed successively with cold 10% aqueous triethylamine solution, cold aqueous HCl solution, cold saturated aqueous bicarbonate solution, and finally saturated aqueous brine solution. The organic phase is dried, filtered, and concentrated in vacuo below 55° C.±5° C. until a solid/liquid slurry containing intermediate (6) is obtained. The slurry is used crude in subsequent reaction without further characterization.

(3S,5S)-(1-Benzyl-5-methyl-piperidin-3-yl)-carbamic acid tert-butyl ester (7). A 50 L reactor is charged with 9.1 Kg of neat benzylamine. The reactor is brought to 55° C. and a solution of intermediate (6) (8.2 Kg) in 1,2-dimethoxyethane (DME) (14.1 Kg) is added to the reactor while maintaining a temperature of 60° C.±5° C. After complete addition of this solution, the reaction is stirred at 60° C.±5° C. for several hours and monitored for completion by TLC or HPLC. The reaction is cooled to ambient temperature and volatiles (DME) are removed by rotary evaporation under vacuum. The residue is diluted with 11.7 Kg of 15% (v/v) ethyl acetate/hexanes solution and treated, while agitating, with 18.7 Kg of 20% (wt) aqueous potassium carbonate solution. A triphasic mixture is obtained upon settling. The bottom aqueous phase is removed and the middle phase is set aside. The upper organic phase is collected and held for combination with extracts from additional extractions. The isolated middle phase is extracted twice again with 11.7 Kg portions of 15% (v/v) ethyl acetate/hexanes solution, each time combining the extracts with original organic phase. The combined organic extracts are transferred into a rotary evaporator and solvent is removed under vacuum until an oily residue remains. The residue is then purified via large-scale preparative chromatography to afford purified intermediate (7) as an oil.

(3S,5S)-(5-Methyl-piperidin-3-yl)-carbamic acid tert-butyl ester (8). A 40 L pressure vessel is charged with 0.6 Kg 50% wet, solid palladium on carbon (E101, 10 wt. %) under flow of nitrogen. A solution of 3.2 Kg intermediate (7) in 13.7 Kg of absolute ethanol is then charged to the reactor under nitrogen. The reactor is purged with nitrogen and is then pressurized with hydrogen at 45 psi. The reaction is then heated to 45° C. while maintaining a hydrogen pressure of 45 psi. The reaction is monitored by TLC or LC until complete. The reaction is cooled to ambient temperature, vented, and purged with nitrogen. The reactor contents are filtered through a bed of Celite and the solids are washed with 2.8 Kg of absolute ethanol. The filtrate is concentrated by rotary evaporation under vacuum until a waxy solid is obtained to afford intermediate (8): TLC R$_f$(Silica F$_{254}$, 70:30 v/v ethyl acetate-hexanes, KMnO$_4$ stain)=0.12; $^1$H NMR (300 MHz, CDCl$_3$) δ 5.31 (br s, 1H), 3.80-3.68 (m, 1H), 2.92 (d, J=11.4 Hz, 1H), 2.77 (AB quart, J$_{AB}$=12.0 Hz, Δν=50.2 Hz, 2H), 2.19 (t, J=10.7 Hz, 1H), 1.82-1.68 (m, 2H), 1.54 (br s, 1H), 1.43 (s, 9H), 1.25-1.15 (m, 1H), 0.83 (d, J=6.6 Hz, 3H); $^{13}$C NMR (75 MHz, CDCl$_3$) δ 155.3, 78.9, 54.3, 50.8, 45.3, 37.9, 28.4, 27.1, 19.2; MS (ESI+) m/z 215 (M+H), 429 (2M+H).

B. Synthesis of 1-Cyclopropyl-7-fluoro-8-methoxy-4-oxo-1,4-dihydro-quinoline-3-carboxylic acid (19)

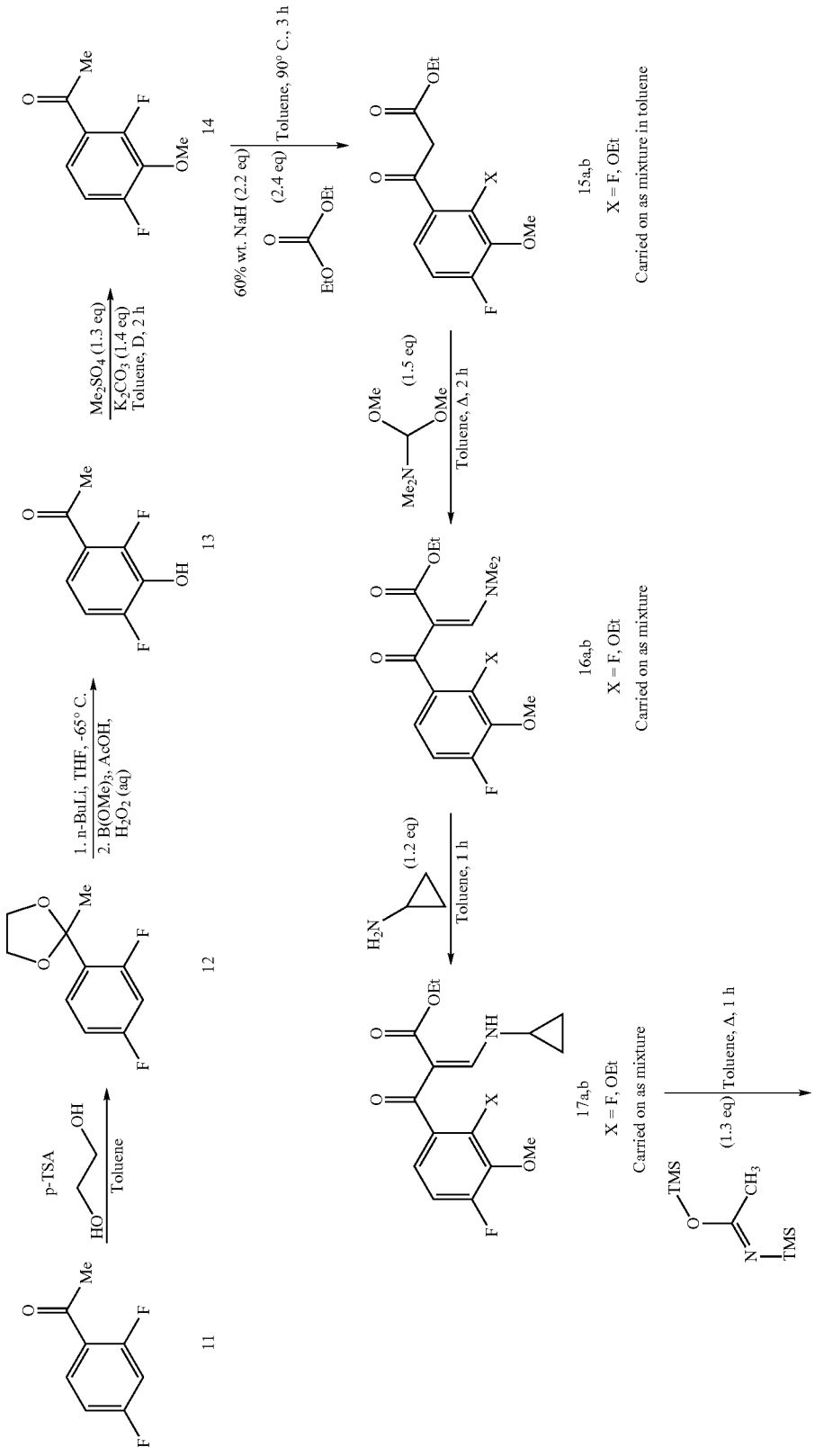

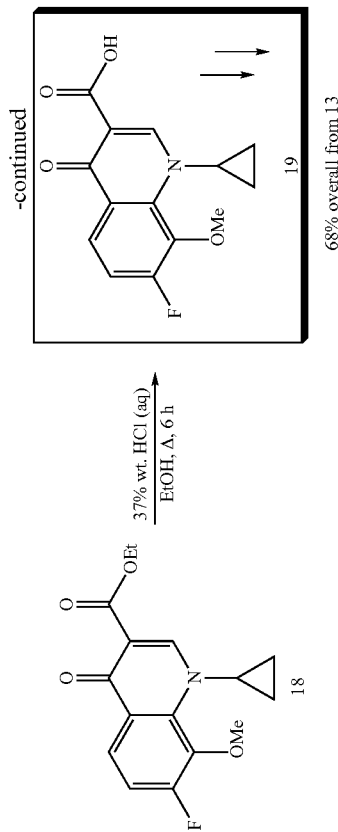

Intermediate (12)

A reactor is charged with a solution of intermediate (11) (1.2 Kg, 7.7 mol, 1.0 eq) in anhydrous toluene (12 L) followed by ethylene glycol (1.8 L, 15.7 mol, 4.2 eq) and solid p-toluenesulfonic acid (120 g, 10 wt. %). The reaction mixture is stirred at ambient temperature for at least 30 minutes and then heated to reflux, collecting the water/toluene azeotrope in a Dean Stark type trap apparatus until the reaction is complete as determined by TLC analysis (15% EtOAc/Hexanes v/v). Upon completion, the reaction is cooled to ambient temperature and poured into an aqueous solution of sodium bicarbonate (6 L). The organic toluene phase was removed and washed with saturated sodium bicarbonate solution (6 L), distilled water (2×6 L), and saturated aqueous brine (6 L). The organic phase was removed and dried over $MgSO_4$, filtered, and evaporated under reduced pressure to afford intermediate (12) as an oil (1.3 Kg, 86%). The material is used without further purification in subsequent reaction steps.

Intermediate (13)

A reactor is charged with a solution of intermediate (12) (1.2 Kg, 6.0 mol, 1.0 eq) in anhydrous tetrahydrofuran (12 L) and n-butyllithium (2.5M in hexanes, 2.6 L, 6.6 mol, 1.1 eq) is added at −40° C., while maintaining this temperature throughout the addition. The reaction is stirred for at least one hour at −40° C. and trimethylborate (0.9 L, 7.8 mol, 1.3 eq) is added to the mixture while maintaining the temperature at or below −40° C. The reaction mixture is stirred for at least one hour at −40° C. until complete as determined by TLC analysis (30% EtOAc/Hexanes v/v). The reaction is warmed slightly to −30° C. and acetic acid (3 L) is added slowly. Upon complete addition, water is added (0.5 L) to the reaction and the mixture is allowed to quickly warm to ambient temperature while stirring overnight. Organic solvent is removed from the reaction by distillation under reduced pressure at 45° C. To the reaction residue is added 3-4 volumes of water (6 L) and 30% hydrogen peroxide (0.7 L, 1.0 eq) slowly at ambient temperature with cooling provided to control the exotherm. The reaction is stirred for at least an hour at ambient temperature until complete as determined by TLC (15% EtOAc/ Hexanes v/v). The reaction mixture is cooled to 0-5° C. and excess peroxide is quenched with the addition of 10% aqueous sodium bisulfite solution (2 L). The mixture is tested to ensure a negative peroxide result and the reaction is acidified by the addition of 6N HCl (aq) (1.2 L). The reaction is stirred until the hydrolysis reaction is complete as determined by TLC or NMR analysis. The resulting solids are collected by suction filtration to afford intermediate (13) as a yellow solid (1.0 Kg, 79%).

Intermediate (14)

A reactor is charged with intermediate (13) (0.53 Kg, 3.0 mol, 1.0 eq) and dissolved in dry toluene (2.7 Kg, 3.1 L). To this solution is added dimethylsulfate (0.49 Kg, 3.9 mol, 1.30 eq) followed by solid potassium carbonate (0.58 Kg, 4.2 mol, 1.4 eq). The reaction mixture is heated to reflux and held for at least 1 hour until complete as determined by HPLC. During this time, vigorous gas evolution is observed. The reaction is then cooled to ambient temperature and diluted with distilled water (3.2 L) along with 30% NaOH (aq) (0.13 Kg, 0.33 eq). The aqueous phase is separated and the remaining toluene phase is extracted twice more with distilled water (3.2 L) combined with 30% NaOH (aq) (0.13 Kg, 0.33 eq), removing the aqueous phase each time. The organic upper phase is concentrated by distillation in vacuo (<100 mbar) at approximately 40° C. until a concentrated toluene solution is achieved. The resulting solution is cooled to ambient temperature, checked for quality and yield by HPLC, and carried forward to the next step in the synthesis without further purification (theoretical yield for intermediate (14) assumed, 0.56 Kg).

Intermediate (15a,b)

A reactor is charged with 1.8 Kg (2.1 L) anhydrous toluene along with sodium hydride (0.26 Kg, 6.6 mol, 2.20 eq) as a 60 wt. % dispersion in mineral oil. To this mixture is added (0.85 Kg, 7.2 mol, 2.4 eq) diethylcarbonate as the reaction mixture is heated to 90° C. over 1 hour. A solution of intermediate (14) (~1.0 eq) in toluene from the previous step is added to the reaction while maintaining a temperature of 90° C.±5° C. Gas evolution can be observed during this addition. After complete addition, the reaction is stirred for at least 30 minutes or until complete as determined by HPLC analysis. Upon completion, the mixture is cooled to ambient temperature and diluted with 10 wt. % aqueous sulfuric acid (3.8 Kg, 3.9 mol, 1.3 eq) with agitation. The phases are allowed to separate and the lower aqueous phase is removed. The remaining organic phase is concentrated in vacuo (<100 mbar) at approximately 40° C. until a concentrated toluene solution is achieved. The resulting solution is cooled to ambient temperature and carried forward to the next step in the synthesis without further purification (theoretical yield for intermediate (15a,b) assumed, 0.85 Kg).

Intermediate (16a,b; 17a,b): A reactor is charged with a solution of intermediate (15a,b) (0.85 Kg, ~3.0 mol, ~1.0 eq) in toluene from the previous step. To the reactor is then added dimethylformamide-dimethylacetal (0.54 Kg, 4.5 mol, 1.5 eq) and the resulting solution is heated to reflux temperature (~95-105° C.). The lower boiling solvent (methanol from reaction) is allowed to distill off while the temperature is maintained at ≧90° C. Heating is continued for at least 1 hour or until complete as determined by HPLC analysis. Upon completion, the reaction containing the mixture of intermediate (16a,b), is cooled to ambient temperature and toluene (1.8 Kg, 2.1 L) along with cyclopropylamine (0.21 Kg, 3.6 mol, 1.2 eq) are added to the reaction. The reaction is stirred at ambient temperature for at least 30 minutes until complete as determined by HPLC. Upon completion, the reaction is diluted with 10 wt. % aqueous sulfuric acid (2.9 Kg, 3.0 mol, 1.0 eq) with agitation, and the phases are then allowed to separate. The aqueous phase is removed and the organic phase is concentrated under reduced pressure (<100 mbar) at approximately 40° C. by distillation. When the desired concentration is achieved, the solution is cooled to ambient temperature and the toluene solution containing the mixture of intermediate (17a,b) is carried forward to the next step in the synthesis without further purification (theoretical yield for intermediate (17a,b) assumed, ~1.1 Kg).

Intermediate (18)

A reactor is charged with a solution of the mixture of intermediate (17a,b) (~4.7 Kg, ~3.0 mol) at ambient temperature. To the reactor is added N,O-bis(trimethylsilyl)acetamide (0.61 Kg, 3.0 mol, 1.0 eq) and the reaction is heated to reflux temperature (~105-115° C.) for at least 30 minutes or until complete as determined by HPLC analysis. If not complete, an additional amount of N,O-bis(trimethylsilyl)acetamide (0.18 Kg, 0.9 mol, 0.3 eq) is added to the reaction to achieve completion. Upon completion, the reaction is cooled to below 40° C. and organic solvent is removed under reduced pressure (<100 mbar) at approximately 40° C. by distillation until a precipitate is formed. The reaction is cooled to ambient temperature and the precipitated solids are isolated by suction filtration and washed with distilled water twice (1×1.8 L, 1×0.9 L). The solid is dried to afford intermediate (18) as a white solid (0.76 Kg, 82%). The material is used without further purification in the next reaction step.

17

Intermediate (19)

A reactor is charged with solid intermediate (18) (0.76 Kg, ~2.5 mol, ~1.0 eq) at ambient temperature followed by ethanol (5.3 Kg, 6.8 L) and 32 wt. % aqueous hydrochloric acid (1.1 Kg, 10 mol). The reaction mixture is brought to reflux temperature (76-80° C.) during which time the mixture first becomes homogeneous and later becomes heterogeneous. The mixture is heated at reflux for at least 5 hours or until complete as determined by TLC analysis (15% EtOAc/Hexanes v/v). Upon completion, the reaction is cooled to 0° C.±5° C. and the precipitated solid is isolated by filtration and washed with distilled water (1.7 Kg) followed by ethanol (1.7 Kg). The isolated solid is dried to afford intermediate (19) as a white solid (0.65 Kg, ~95%). $^1$H NMR (CDCl$_3$, 300 MHz) δ (ppm): 14.58 (s, 1H), 8.9 (s, 1H), 8.25 (m, 1H), 7.35 (m, 1H), 4.35 (m, 1H), 4.08 (s, 3H), 1.3 (m, 2H), 1.1 (m, 2H) $^{19}$F NMR (CDCl$_3$+CFCl$_3$, 292 MHz) δ (ppm): −119. HPLC: 99.5% by area.

C. Synthesis of borone ester chelate of 1-Cyclopropyl-7-fluoro-8-methoxy-4-oxo-1,4-dihydro-quinoline-3-carboxylic acid (20)

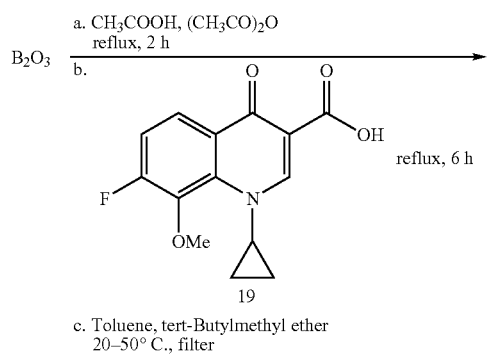

18

A reactor is charged with boron oxide (2.0 Kg, 29 mol) followed by dilution with glacial acetic acid (8.1 L, 142 mol) and acetic anhydride (16.2 L, 171 mol). The resulting mixture is heated to reflux temperature for at least 2 hours. The reaction contents are cooled to 40° C. and the solid 7-fluoroquinolone acid intermediate (19) (14.2 Kg, 51 mol) is added to the reaction mixture. The mixture is again heated to reflux temperature for at least 6 hours. Reaction progress is monitored by HPLC and NMR. The mixture is cooled to approximately 90° C. and toluene (45 L) is added to the reaction. The reaction is further cooled to 50° C. and tert-butylmethyl ether (19 L) is added to the reaction mixture to bring about precipitation of the product. The mixture is then cooled to 20° C. and the solid product 19 is isolated by filtration. The isolated solids are then washed with tert-butylmethyl ether (26 L) prior to drying in a vacuum oven at 40° C. (50 torr). The product yield obtained for intermediate (20) in this reaction is 86.4%. Raman (cm$^{-1}$): 3084.7, 3022.3, 2930.8, 1709.2, 1620.8, 1548.5, 1468.0, 1397.7, 1368.3, 1338.5, 1201.5, 955.3, 653.9, 580.7, 552.8, 384.0, 305.8. NMR (CDCl$_3$, 300 MHz) δ (ppm): 9.22 (s, 1H), 8.38-8.33 (m, 1H), 7.54 (t, J=9.8 Hz, 1H), 4.38-4.35 (m, 1H), 4.13 (s, 3H), 2.04 (s, 6H), 1.42-1.38 (m, 2H), 1.34-1.29 (m, 2H). TLC (Whatman MKC18F Silica, 60Å, 200 μm), Mobile Phase: 1:1 (v/v) CH$_3$CN:0.5N NaCl (aq), UV (254/366 nm) visualization; R$_f$=0.4-0.5.

D. Coupling of 1-Cyclopropyl-7-fluoro-8-methoxy-4-oxo-1,4-dihydro-quinoline-3-carboxylic acid (20) to (3S,5S)-(5-Methyl-piperidin-3-yl)-carbamic acid tert-butyl ester (8), and synthesis of malate salt of (3S,5S)-7-[3-amino-5-methyl-piperidinyl]-1-cyclopropyl-1,4-dihydro-8-methoxy-4-oxo-3-quinolinecarboxylic acid (25)

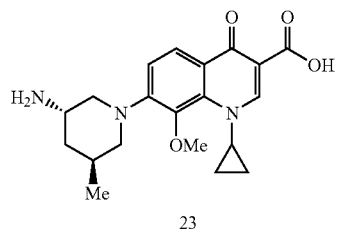

23

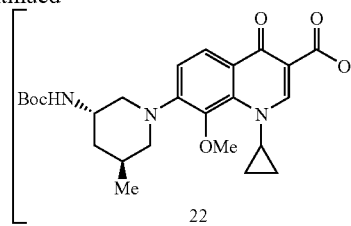

22 Not isolated a. d,l-Malic acid

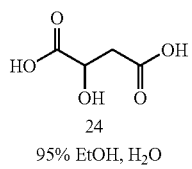

24
95% EtOH, H₂O

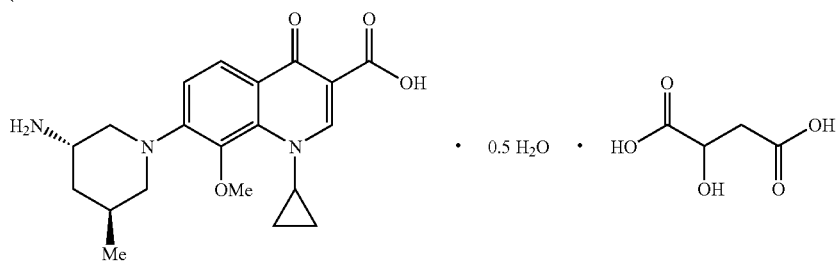

25

A reactor is charged with solid intermediate (20) (4.4 Kg, 10.9 mol) followed by dilution with a solution of triethylamine (TEA) (2.1 L, 14.8 mol) and piperidine side chain intermediate (8) (2.1 Kg, 9.8 mol) in acetonitrile (33.5 L, 15.7 L/Kg) at room temperature. The resulting mixture is warmed to approximately 50° C. until reaction is judged complete. Reaction progress is monitored by HPLC or reverse phase TLC. When complete, the reaction is cooled to approximately 35° C. and reaction volume is reduced to approximately half by distillation of acetonitrile under vacuum between 0-400 torr. The reactor is then charged with 28.2 Kg of 3.0N NaOH (aq) solution and the temperature is raised to approximately 40° C. Distillation under vacuum is continued between 1-4 hours or until no further distillates are observed. The reaction is then cooled to room temperature and the hydrolysis reaction is monitored by HPLC or reverse phase TLC. Upon completion, the reaction mixture is neutralized to a pH of between 6-8 by adding ~4-5 Kg of glacial acetic acid. The reactor is then charged with 12.7 Kg (9.6 L) of dichloromethane as an extraction solvent, the mixture is agitated, phases are allowed to separate, and the organic dichloromethane phase is removed. The extraction process is repeated two additional times using 12.7 Kg (9.6 L) of dichloromethane, collecting the lower, organic phase each time. The aqueous phase is discarded and the organic extracts are combined in a single reactor. The reactor contents are heated to 40° C. and the reaction volume is reduced to approximately one half by distillation. The reactor is then charged with 20.2 Kg 6.0N HCl (aq) solution, the temperature is adjusted to 35° C., and agitation is allowed for at least 12 hours to permit the Boc deprotection reaction to occur. The reaction is monitored by HPLC or reverse phase TLC. When complete, agitation is discontinued and the phases are allowed to separate. The lower, organic phase is removed and set aside. The reactor is then charged with 12.7 Kg (9.6 L) of dichloromethane as an extraction solvent, the mixture is agitated, phases are allowed to separate, and the organic dichloromethane phase is removed. The organic extracts are combined and discarded. The remaining aqueous phase is diluted with 18.3 Kg distilled water and the temperature is raised to approximately 50° C. Distillation under vacuum (100-400 torr) is performed to remove residual dichloromethane from the reaction. The pH of the reaction is then adjusted to between 7.8-8.1 using about 9.42 Kg of 3.0N NaOH (aq) solution while keeping the temperature of the reaction below 65° C. The reaction is cooled to 50° C. and the precipitated solids are aged for at least an hour prior to cooling the mixture to room temperature. The solids are isolated by suction filtration and washed twice with 5.2 Kg portions of distilled water. The solids are dried for at least 12 hours with suction and then for an additional 12 hours in a convection oven at 55° C. The yield achieved for intermediate (23) in this example is 3.2 Kg (79%). A reactor is charged with 3.2 Kg solid intermediate (23) and the solids are suspended in 25.6 Kg of 95% ethanol as solvent. To the reactor is then added 1.1 Kg of solid D,L-malic acid (24), and the mixture is heated to reflux temperature (~80° C.). Distilled water (~5.7 L) is added to the reaction until a complete solution is achieved and 0.2 Kg of activated charcoal is added. The reaction mixture is passed through a filter to achieve clarification, cooled to 45° C. and held for a period of at least 2 hours to allow crystallization to occur. The reaction mixture is further cooled to 5° C. and the suspended solids are isolated by suction filtration. The solids are then washed with 6.6 KG of 95% ethanol and dried for at least 4 hours with suction under vacuum. The solids are then further dried in a convection oven for at least 12 hours at 45° C. to afford 3.1Kg of compound (25) (70%). NMR (D₂O, 300 MHz)δ (ppm):8.54 (s, 1H), 7.37 (d, J=9.0 Hz, 1H), 7.05 (d, J=9.0 Hz, 1H), 4.23-4.18 (m, 1H), 4.10-3.89 (m, 1H), 3.66 (br s, 1H), 3.58 (s, 3H), 3.45 (d, J=9.0 Hz, 1H), 3.34 (d, J=9.3 Hz, 1H), 3.16 (d, J=12.9 Hz, 1H), 2.65

(dd, J=16.1, 4.1 Hz, 1H), 2.64-2.53 (m, 1H), 2.46 (dd, J=16.1, 8.0 Hz, 1H), 2.06 (br s, 1H), 1.87 (d, J=14.4 Hz, 1H), 1.58-1.45 (m, 1H), 1.15-0.95 (m, 2H), 0.91 (d, J=6.3 Hz, 3H); 0.85-0.78 (m, 2H). TLC (Whatman MKC18F Silica, 60Å, 200 μm), Mobile Phase: 1:1 (v/v) $CH_3CN$: 0.5N NaCl (aq), UV (254/366 nm) visualization. HPLC: Mobile Phase $H_2$ with 0.1% formic acid/Acetonitrile with 0.1% formic acid, gradient elution with 88% $H_2O$/formic acid to 20% $H_2O$/formic acid, Zorbax SB-C8 4.6 mm×150 mm column, Part No. 883975.906, 1.5 ml/min rate, 20 min run time, 292 nm, Detector Model G1314A, S/N JP72003849, Quat Pump Model G1311A, S/N US72102299, Auto Sampler Model G1313A, S/N DE14918139, Degasser Model G1322A, S/N JP73007229; approximate retention time for intermediate (19): 13.0 min; approximate retention time for intermediate (20): 11.6 min; approximate retention time for intermediate (21): 16.3 min; approximate retention time for intermediate (22): 18.2 min; approximate retention time for intermediate (23): 8.6 min; approximate retention time for compound (25): 8.6 min.

Example 2

Preparation of Salt and Evaluation of Salt Forms

A salt screen is performed on 100 mg of free base. The isolated salt forms are evaluated by NMR, elemental analysis, TG-DTA, XRD, & HPLC. Table 1 describes physical and chemical characteristics of these salt forms. As shown, the malate salts may provide a balance between desired solubility, stability, and ease of isolation. In addition, use of malate salts may help with chiral purification. Further, D,L-malate, D-malate or L-malate salt may provide differing advantages depending upon the nature of the chiral impurity to be removed. The hydrated forms may provide better water moisture and solid-state stability as well as greater ease of isolation. Use of the anhydrous forms may enhance apparent solubility and dissolution rate. Thus, the malate salts of Compound I exhibit certain advantages, including the ease of isolation, reduced hygroscopicity, greater solubility in water, greater stability, and ease of formulation.

Example 3

Preparation of D,L-Malate Hemi-Hydrate Salt of Compound I

A. Synthesis of D,L-malate salt of compound I from free base: Ten grams of free base of compound I and one equivalent of D,L-malic acid are heated in 105 mL of 95% ethanol to reflux (approximately 78° C.). Fifteen mL water is added while maintaining the temperature near 78° C. Stirring and heating is continued until the completely dissolved. Additional water may be added to ensure complete dissolution. The solution is cooled slowly (at least 3 hours) to room temperature while stirring to initiate crystallization. If an oily or waxy mass (or a phase other than hemi-hydrate) precipitates, the solution is reheated to dissolve the precipitate completely and is cooled more slowly. Crystalline solids are then filtered and washed with a small volume of 95% ethanol. The crystals are dried at ambient pressure, room temperature at a relative humidity of 25%-75% RH.

B. Crystallization of existing malate salt of compound I: Ten grams of D,L-malate salt of compound I is heated in 105 mL of 95% ethanol to reflux (approximately 78° C.). Fifteen mL of water is added while maintaining the temperature near 78° C. Stirring and heating is continued until the salt is completely dissolved. Additional water may be added to ensure complete dissolution. The solution is cooled slowly (at least about 3 hours) to room temperature while stirring to initiate crystallization. If an oily or waxy mass (or a phase other than hemi-hydrate) precipitates, the solution is reheated to dissolve the precipitate completely and is cooled more slowly. Crystalline solids are then filtered and washed with a small volume of 95% ethanol. The crystals are dried at ambient pressure, room temperature at a relative humidity of 25%-75% RH.

Example 4

Preparation of D-Malate Hydrate Salt of Compound I

A. Synthesis of D-malate salt of compound I from free base: Ten grams of free base of compound I and one equiva-

TABLE 1

| Salt form | Solubility (mg/ml) | Ease of Isolation | Control of salt stoichiometry | Control of hydration state and polymorphism | Comments |
| --- | --- | --- | --- | --- | --- |
| DL-malate, hemi-hydrate, anhydrate | 12 (hemi-hydrate) | Ready isolation | Reliable | Easy to control. | Ease and reliability of isolation |
| Tosylate | 2 | Ready isolation | Reliable | Two phases identified | Lower solubility |
| Freebase | <1 | Tendency of one phase to gel | N/A | Two phases identified | Lower solubility, difficult to isolate |
| L-Tartrate | 7 | Ready isolation | Reliable | Three phases identified | Difficult to control final solid-state form |
| Fumarate | 9 | Ready isolation | Reliable | At least two phases identified. | Difficult to control final solid-state form |
| L-Glutamate | >160 | Difficult to isolate | May contain freebase | Not done | Difficult to isolate as a solid form |
| D-Glucuronate | 8 | Degradation | Reliable | Single phase observed | Degradation upon scale up |
| HCl | Not determined | Ready Isolation | Mixed salts observed | At least two phases observed, hygroscopic phase | Difficult to control final solid-state form |
| Maleate | | Not isolated | | | Not able to isolate as a solid |
| Mesylate | | Not isolated | | | Not able to isolate as a solid |
| Lactate | | Not isolated | | | Not able to isolate as a solid |
| Citrate | | Not isolated | | | Not able to isolate as a solid | lent of D-malic acid are heated in 75 mL of 95% ethanol to reflux (approximately 78° C.). Twenty-five mL water is added while maintaining the temperature near 78° C. Stirring and heating is continued until the completely dissolved. Additional water may be added to ensure complete dissolution. The solution is cooled slowly (at least 3 hours) to room temperature while stirring to initiate crystallization. If an oily or waxy mass (or a phase other than hydrate), the solution is reheated to dissolve the precipitate completely and is cooled more slowly. Crystalline solids are then filtered and washed with a small volume of 95% ethanol. The crystals are dried at ambient pressure, room temperature at a relative humidity of 25%-75% RH.

B. Crystallization of existing D-malate salt of compound I: Ten grams of D-malate salt of compound I is heated in 75 mL of 95% ethanol to reflux (approximately 78° C.). Twenty-five mL of water is added while maintaining the temperature near 78° C. Stirring and heating is continued until the salt is completely dissolved. Additional water may be added to ensure complete dissolution. The solution is cooled slowly (at least 3 hours) to room temperature while stirring to initiate crystallization. If an oily or waxy mass (or a phase other than hydrate) precipitates, the solution is reheated to dissolve the precipitate completely and is cooled more slowly. Crystalline solids are then filtered and washed with a small volume of 95% ethanol. The crystals are dried at ambient pressure, room temperature at a relative humidity of 25%-75% RH.

Example 5

Preparation of L-Malate Hydrate of Compound I

A. Synthesis of L-malate salt of compound I from free base: Ten grams of free base of compound I and one equivalent of L-malic acid are heated in 75 mL of 95% ethanol to reflux (approximately 78° C.). Twenty-five mL water is added while maintaining the temperature near 78° C. Stirring and heating is continued until the completely dissolved. Additional water may be added to ensure complete dissolution. The solution is cooled slowly (at least 3 hours) to room temperature while stirring to initiate crystallization. If an oily or waxy mass (or a phase other than hydrate) precipitates, the solution is reheated to dissolve the precipitate completely and is cooled more slowly. Crystalline solids are then filtered and washed with a small volume of 95% ethanol. The crystals are dried at ambient pressure, room temperature at a relative humidity of 25%-75% RH.

B. Crystallization of existing L-malate salt of compound I: Ten grams of L-malate salt of compound I is heated in 75 mL of 95% ethanol to reflux (approximately 78° C.). Twenty-five mL of water is added while maintaining the temperature near 78° C. Stirring and heating is continued until the salt is completely dissolved. Additional water may be added to ensure complete dissolution. The solution is cooled slowly (at least 3 hours) to room temperature while stirring to initiate crystallization. If an oily or waxy mass (or a phase other than hydrate) precipitates, the solution is reheated to dissolve the precipitate completely and is cooled more slowly. Crystalline solids are then filtered and washed with a small volume of 95% ethanol. The crystals are dried at ambient pressure, room temperature at a relative humidity of 25%-75% RH.

Example 6

Preparation of D-Malate Anhydrate Salt of Compound I 280 mg of D-malate hydrate salt of compound I is heated in 5 mL dry methanol to 70° C. Heating and stifling is continued until the salt is completely dissolved. The solution is then allowed to cool slowly to room temperature with stirring (taking at least about 3 hours to cool). The crystals are filtered and dried under a dry nitrogen purge to protect the sample from moisture during the drying process.

Example 7

Preparation of L-Malate Anhydrate Salt of Compound I 200 mg L-malate hydrate salt of compound I is heated in 2 mL dry methanol to 70° C. Heating and stirring are continued until the salt is completely dissolved. The solution is allowed to cool very slowly to room temperature. The solution is stirred for extended period until crystallization occurs, or the solution is evaporated with dry nitrogen to induce more rapid crystallization to protect material from water gain during the crystallization and isolation stages.

Example 8

Analyses of the Polymorphs

Various polymorphs that may be obtained using the methods described above may be further characterized using the techniques described below.

Water content is determined by Thermogravimetric Analysis (TG). A Perkin-Elmer TGA-7 is used to generate water assays. Samples (5-12 mg) are run under dry nitrogen in open aluminum sample pans at a scan rate of 5° C./minute.

Moisture contents observed for the hemihydrate and hydrates, as received, ranges from 1.5% to 3.0%. Hydrates and hemihydrates may be dried to lower water contents and may still maintain the spectroscopy and XRD signatures of the fully hydrated materials. Moisture contents observed for the anhydrates ranged from none detected to 1.0%

X-ray Diffraction analysis: X-ray powder diffraction is performed on the samples using a Bruker D5000 X-Ray diffractometer. The D5000 is equipped with a 2.2 kW Cu anode X-ray tube, an Anton Parr TTK-1 low temperature stage, and high speed position sensitive detector (PSD). Cu K radiation (=1.5418 Å) is used to obtain powder patterns. A dual foil, nickel filter is placed in the receiving path of the X-Rays to remove the K β-radiation. Material is mounted and analyzed on a front loading sample holder. Scans are performed over the range of 3.5-40 2 theta, at a 0.02 step size for 0.2 seconds per step.

Solid-state Nuclear Magnetic Resonance (SSNMR) analysis: All data are recorded on a Varian 300 Unity Inova spectrometer equipped with a 7 mm CPMAS probe spinning at 5 kHz. The 75.4 MHz $^{13}$C spectra are recorded with the cross-polarization magic angle spinning (CP/MAS) TOSS (Total Suppression of Spinning Sideband) experiment. The samples are not ground but packed directly into 7 mm silicon nitride rotors.

Infrared (IR) analysis: The samples are analyzed by split mull technique using a BioRad FTS-3000 FTIR spectrometer with a KBr beamsplitter. Sixteen background and sample scans are obtained for each sample at 4 wavenumber resolution. Sample prep consist of mixing about 1% sample with the appropriate mulling agent (e.g., fluorolube for 4000-1350 wavenumbers, nujol for 1350-450 wavenumbers) using a agate mortar and pestle. The samples may not be ground prior to mixing with the mulling agent. The background scans are obtained using the corresponding KBr discs for which the mulled sample is sandwiched for sample analysis.

Example 9

Characteristics of Various Salt Forms

Malate salts of 7-[3S-amino-5S-methyl-piperidinyl]-1-cyclopropyl-1,4-dihydro-8-methoxy-4-oxo-3-quinolinecarboxylic acid may be formed and isolated under practical manufacturing conditions. Use of the chiral malate for salt formation (as the racemic mix or the chirally pure forms) may in some instances assist with chiral purification of 7-[3S-amino-5S-methyl-piperidinyl]-1-cyclopropyl-1,4-dihydro-8-methoxy-4-oxo-3-quinolinecarboxylic acid. As a class, the malate salts are soluble to sparingly soluble in water (per the US Pharmacopoeia 28 definition) and exhibit favorable chemical stability. The hydrated forms exhibit phase stability for relative humidities up to 75% relative humidity as measured by dynamic vapor sorption methods and via static humidity chamber studies. Using the same test methods, the anhydrate forms are shown to pick up moisture and spontaneously convert to the corresponding hydrated form upon exposure to humidity.

D,L-Malate Hemi-Hydrate Salt of Compound I

The structure for the D,L-malate hemi-hydrate is definitively confirmed by single crystal X-ray diffraction. The smallest unit of this moiety consists of two molecules of 7-[3S-amino-5S-methyl-piperidinyl]-1-cyclopropyl-1,4-dihydro-8-methoxy-4-oxo-3-quinolinecarboxylic acid, one molecule of D-malic acid, one molecule of L-malic acid and one molecule of water. The water hydration is of a channel nature resulting in some variation of water content with relative humidity.

D-Malate Hydrate and L-Malate Hydrate Salts of Compound I

D-Malate Hydrate and L-Malate Hydrate may be readily isolated as crystalline solids from aqueous solvent systems. Successful isolation requires use of the chirally pure acid. Like the D,L-Malate Hemi-hydrate, the water of hydration appears to be channel like with water content somewhat dependent upon relative humidity.

D-Malate Anhydrate and L-Malate Anhydrate Salts of Compound I

Neither form of the anhydrates has been isolated with crystallites of sufficient size to generate high quality X-ray diffraction patterns. Isolation of the anhydrates often results in an oil or wax that slowly crystallizes into a material of high surface area. The anhydrates produce powder patterns that are consistent with nano-crystalline material. The resulting X-ray diffraction patterns have very low signal and irresolvable peaks. The nano-crystalline, high surface area anhydrates convert to the corresponding hydrate forms upon exposure to humidity.

Except as otherwise noted, all amounts including quantities, percentages, portions, and proportions, are understood to be modified by the word "about", and amounts are not intended to indicate significant digits.

Except as otherwise noted, the articles "a", "an", and "the" mean "one or more".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications may be made without departing from the spirit and scope of the invention. It is therefore intended to cover in the appended claims all such changes and modifications that are within the scope of this invention.

What is claimed is:

1. A D,L-malate hemi-hydrate salt of (3S,5S)-7-[3-amino-5-methyl-piperidinyl]-1-cyclopropyl-1,4-dihydro-8-methoxy-4-oxo-3-quinolinecarboxylic acid.

2. The D,L-malate hemi-hydrate salt according to claim 1, having an X-ray diffraction pattern substantially in accordance with the pattern of FIG. 1.

3. The D,L-malate hemi-hydrate salt according to claim 1, having a solid-state $^{13}C$ NMR spectrum substantially in accordance with the pattern of FIG. 4.

4. The D,L-malate hemi-hydrate salt according to claim 1, having an infrared spectrum pattern substantially in accordance with the pattern of FIG. 9.

5. The D,L-malate hemi-hydrate salt according to claim 2, having characteristic X-ray diffraction peaks at about 10.7, about 11.98 and about 12.5 degrees 2 theta.

6. A D-malate hydrate salt of (3S,5S)-7-[3-amino-5-methyl-piperidinyl]-1-cyclopropyl-1,4-dihydro-8-methoxy-4-oxo-3-quinolinecarboxylic acid having an X-ray diffraction pattern substantially in accordance with the pattern of FIG. 2.

7. An L-malate hydrate salt of (3S,5S)-7-[3-amino-5-methyl-piperidinyl]-1-cyclopropyl-1,4-dihydro-8-methoxy-4-oxo-3-quinolinecarboxylic acid having an X-ray diffraction pattern substantially in accordance with the pattern of FIG. 3.

8. A D-malate anhydrate salt of (3S,5S)-7-[3-amino-5-methyl-piperidinyl]-1-cyclopropyl-1,4-dihydro-8-methoxy-4-oxo-3-quinolinecarboxylic acid having a solid-state $^{13}C$ NMR spectrum substantially in accordance with the pattern of FIG. 7.

9. An L-malate anhydrate salt of (3S,5S)-7-[3-amino-5-methyl-piperidinyl]-1-cyclopropyl-1,4-dihydro-8-methoxy-4-oxo-3-quinolinecarboxylic acid having a solid-state $^{13}C$ NMR spectrum substantially in accordance with the pattern of FIG. 8.

10. The D-malate hydrate salt according to claim 6, having a solid-state $^{13}C$ NMR spectrum substantially in accordance with the pattern of FIG. 5.

11. The D-malate hydrate salt according to claim 6, having an infrared spectrum pattern substantially in accordance with the pattern of FIG. 10.

12. The D-malate hydrate salt according to claim 6, having characteristic X-ray diffraction peaks at about 9.3, about 12.1 and about 22.6 degrees 2 theta.

13. The L-malate hydrate salt according to claim 7, having a solid-state $^{13}C$ NMR spectrum substantially in accordance with the pattern of FIG. 6.

14. The L-malate hydrate salt according to claim 7, having an infrared spectrum pattern substantially in accordance with the pattern of FIG. 11.

15. The L-malate hydrate salt according to claim 7, having characteristic X-ray diffraction peaks at about 9.5, about 11.7 and about 12.3 degrees 2 theta.

16. The D-malate anhydrate salt according to claim 8, having an infrared spectrum pattern substantially in accordance with the pattern of FIG. 12.

17. The L-malate anhydrate salt according to claim 9, having an infrared spectrum pattern substantially in accordance with the pattern of FIG. 13.

* * * * *